US006772073B2

(12) United States Patent
Freire et al.

(10) Patent No.: US 6,772,073 B2
(45) Date of Patent: Aug. 3, 2004

(54) METHOD FOR PREDICTION OF BINDING TARGETS AND THE DESIGN OF LIGANDS

(75) Inventors: Ernesto Freire, Baltimore, MD (US); Irene Luque, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 57 days.

(21) Appl. No.: 09/734,696

(22) Filed: Dec. 13, 2000

(65) Prior Publication Data

US 2001/0000807 A1 May 3, 2001

Related U.S. Application Data

(62) Division of application No. 09/089,097, filed on Jun. 2, 1998, now Pat. No. 6,226,603.
(60) Provisional application No. 60/066,495, filed on Nov. 24, 1997, and provisional application No. 60/048,274, filed on Jun. 2, 1997.

(51) Int. Cl.$^7$ .............................. G06N 1/00; G06F 17/50
(52) U.S. Cl. ............................................. 702/27; 703/2
(58) Field of Search ................................ 703/2; 702/27

(56) References Cited

U.S. PATENT DOCUMENTS

| 5,331,573 | A | 7/1994 | Balaji et al. ................. 364/500 |
| 5,434,796 | A | 7/1995 | Weininger .................... 364/496 |
| 5,495,423 | A | 2/1996 | DeLisi et al. ................ 364/496 |
| 5,612,895 | A | 3/1997 | Balaji et al. ................. 364/496 |
| 5,642,292 | A | 6/1997 | Itai et al. ..................... 364/496 |
| 5,854,992 | A | 12/1998 | Shakhnovich et al. ......... 702/27 |
| 5,867,402 | A | 2/1999 | Schneider et al. ........... 364/496 |

OTHER PUBLICATIONS

Abdel–Meguid, Sherin et al, "An Orally Bioavailable HIV–1 Protease Inhibitor Containing an Imidazole–Derived Peptide Bond Replacement: Crystallographic and Pharmacokinetic Analysis", *Biochem.*, 1994, 33:11671–77.
Bailey,David et al, "X–Ray–Crystallographic Studies of complexes of Pestatin A and A Statine Containing Human Renin Inhibitor with Exdothiapepsin", *Biochem.*, 1993, 289:363–371.
Baldwin, Eric T. et al, "Structural Basis of Drug Resistance for the V82A Mutant of HIV–1 Proteinase", *Nature Struc. Biol.*, 1995, 2:244–249.
Baldwin, Robert L., "Temperature Dependence of the Hydrophobic Interaction in Protein Folding", *Proc. Nat'l Acad. Sci. USA*, 1986, 83:809–8072.
Bardi, Jason S. et al, "Structure–Based Thermodynamic Analysis of HIV–1 Protease Inhibitors", *Biochem.*, 1997 36:6588–6596.
Blundell, T.L. et al, "X–Ray Analyses of Aspartic Proteinases" "The Three–Dimensional Structure at 2–1 A Resolution of Endiothiapepsin", *J. Mol. Biol.*, 1990, 211:919–941.
Brown, Eric D. et al, "Purification of Two Fungal Aspartic Proteinases Using Fast Protein Liquid Chromatography", *Agric. Biol. Chem.*, 1990, 54:1563–1565.
Cabani, Sergio et al, "Group Contributions to the Thermodynamic Properties of Non–Ionic Organic Solutes in Dilute Aqueous Solution", *J. Sol. Chem.*, 1981, 10:563–595.
Cha, Sungman, "Tight–Binding Inhibitors–I" "Kinetic Behavior", *Biochem. Pharmac.*, 1975, 24:2177–2185.
Condra, Jon H. et al, "In Vivo Emergence of HIV–1 Varants Resistant to Multiple Protease Inhibitors", *Nature*, 1995, 374: 569–570.
D'Aquino, J. Alejando et al, "The Magnitude of the Backbone Conformational Entropy Change in Protein Folding", *Proteins*, 1996, 25:143–156.
Dunn, Ben M. et al, "A Systematic Series of Synthetic Chromophoric Substrates for Aspartic Proteinases", *Biochem. J.*, 1986, 237:899–896.
Erickson, John et al, "Design, Activity, and 2.8 A Crystal Structure of a $C_2$ Symmetric Inhibitor Complexed to HIV–1 Protease", *Science*, 1990, 249:527–529.
Fassler, A. et al, "Novel Psyeudosymmetric Inhibitors of HIV–1 Protease", *Bioorg. Med. Chem. Lett.* 1993, 3:2837–2842.
Freire, Ernesto et al, "Isothermel Titration", *Anal. Chem.*, 1990, 62:950–959.
Freire, Ernesto et al, "Molecular Basis of Co–Operativity in Protein Folding" *J. Mol. Biol.*, 1991, 222:687–698.
Freire, Ernesto, "Perspectives in Biochemistry and Biophysics", *Archives Biochem. Biophys.*, 1993, 303:181–184.

(List continued on next page.)

Primary Examiner—Marjorie Moran
(74) Attorney, Agent, or Firm—Whitham, Curtis & Christofferson, P.C.

(57) ABSTRACT

A computer-based method for the identification of binding targets in proteins and other macromolecules is provided. More particularly, the invention includes an algorithm aimed at predicting binding targets in proteins. This algorithm, named Woolford, requires knowledge of the high resolution structure of the protein but no knowledge of the location or identity of natural binding sites or ligands. Binding targets in the protein are identified and classified according to their expected optimal affinities. Binding targets can be located at the protein surface or at internal surfaces that become exposed as a result of partial unfolding, conformational changes, subunit dissociation, or other events. The entire protein is mapped according to the binding potential of its constituent atoms. Once binding targets are identified, optimal ligands are designed and progressively built by the addition of individual atoms or chemical groups that complement structurally and energetically the selected target. This algorithm is expected to have significant applications in structure-based drug design since it allows: 1) identification of binding targets in proteins; 2) identification of additional targets if the primary target is known; 3) design of ligand molecules with optimal binding affinities for the selected target; and 4) refinement of lead compounds by defining the location and nature of chemical groups for optimal binding affinity.

4 Claims, 25 Drawing Sheets

OTHER PUBLICATIONS

Garcia–Moreno, Bert and E., "Probing Structural and Physical Basis of Protein Energetics Linked to Protons and Salt", *Methods Enzymol.*, 1995, 259:512–528.

Gomez, Javier et al, "The Heat Capacity of Proteins", *Proteins: Structure, Function and Genetics*, 1995, 22:404–412 (1995).

Gomez, Javier et al, "Thermodynamic Mapping of the inhibitor Site of the Aspartic Protease Endothiapepsin", *J. Mol. Biol.*, 1995, 252:337–350.

Gomez, Javier et al, "Structural Thermodynamic Study of the Binding of Renin Inhibitors to Endothiapepsin", "Structure and Function of Aspartic Proteinases: Retroviral and Cellular Enzymes", (Eds. James, M.N.G.), Plenum Publishing Co., New York, 1997.

Hilser, Vincent J. et al, "Structure–based Calculation of the Equilibrium Folding Pathway of Proteins. Correlation with Hydrogen Exchange Protection Factors", *J. Mol. Biol.*, 1996(a) 262, 756–772.

Hilser, Vincent, J. et al, "The Enthalpy Change in Protein Folding and Binding: Refinement of Parameters for Structure–Based Calculations", *Proteins*, 1996, 26:123–133.

Hilser, Vincent, J. et al, "Predicting the Equilibrium Protein Folding Pathway: Structure–Based Analysis of Staphylococcal Nuclease" *Proteins*, 1997(a), 27:117–183.

Hilser, Vincent J. et al, "Structure–based Statistical Thermodynamic Analysis o T4 Lysozyme Mutants: Structural Mapping of Cooperative Interactions" *Biophysical Chem.*, 1997 (b), 64: 69–79.

Ho, David D. et al, "Characterization of Human Immunodeficiency Virus Type 1 Variants with Increased Resistance to a $C_2$–Symmetric Protease Inhibitor", *J. Virol.*, 1994, 68:2016–2020.

Hoog, Susan S., "A Check on Rational Drug Design: Crystal Structure of a Complex of Human Immunodeficiency Virus Type 1 Protease with a Novel γ–Turn Mimetic Inhibitor", *J. Med. Chem.*, 1995, 38:3426–3252.

Hyland, Lawrence, J., "Human Immunodeficiency Virus–1 Protease. 2. Use of pH Rate Studies and Solvent Kinetic Isotope Effects to Elucidate Details of Chemical Mechanism", *Biochemistry*, 1991, 30:8454–8463.

Iijima, Hiroshi et al, "Calibration of Effective Van Der Waals Atomic Contact Radii for Proteins and Peptides", *Proteins*, 1987, 2:330–339.

Janin, Joel et al, "Conformation of Amino Acid Side–Chains in Proteins", *J. Mol. Biol.*, 1978, 125:357–386.

Janin, Joel, "Elusive Affinities", *Proteins*, 1995, 21:30–39.

Kaplan, Andrew, H., "Selection of Multiple Human Immunodeficiency Virus Type 1 Variants that Encode Viral Proteases with Decreased Sensitivity to an Inhibitor of the Viral Protease", *Proc. Natl. Acad. Sci. USA*, 1994, 91:5597–5601.

Kauzmann, W., "Some Factors in the Interpretation of Protein Denaturation", *Adv. Protein Chem.*, 1959, 14:1–63.

Kim, E.E. et al, "Crystal Structure of HIV–1 Protease in Complex with VX–478, a Potent and Orally Bioavailable Inhibitor of the Enzyme" *J. Am. Chem. Soc.*, 1995, 117:1181–1182.

Kuzmic, Petr, "Program DYNAFIT for the Analysis of Enzyme Kinetic Data: Application to HIV Proteinase", *Anal. Biochem.*, 1996, 237:260–273.

Larson, Merle K., "Endothia Parasitcia Protease. Parameters Affecting Activity of the Rennin–Like Enzyme", *J. Dairy Sci.*, 1970, 53:253–261.

Lee, B. et al, "The Interpretation of Protein Structures: Estimates of Static Accessibility", *J. Mol. Biol.*, 1971, 55:379–400.

Lee, Kon Ho et al, "Estimation of Changes in Side Chain Configurational Entropy in Binding and Folding: General Methods and Application to Helix Formation", *Proteins: Struct. Func. and Genetics*, 1994, 20:68–84.

Levitt, Michael, "Energy Refinement of Hen Egg–White Lysozyme", *J. Mol. Biol.*, 1974, 82:393–420.

Lin, Yingzhang et al, "Effect of Point Mutations on the Kinetics and the Inhibition of Human Immunodeficiency Virus Type 1 Protease: Relationship to Drug Resistance", *Biochem.*, 1993, 34:1143–1152.

Luque, Irene et al, "Structure–Based Thermodynamic Scale of β–Helix Propensities in Amino Acids", *Biochemistry*, 1996, 35:13681–13688.

Madhusoodan, Hosur, V. et al, "Influence of Stereochemistry on Activity and Binding Modes for $C_2$ Symmetry–Based Diol Inhibitors of HIV–1 Protease", *J. Am. Chem. Soc.*, 1994, 116:847–855.

Murphy, Kenneth P. et al, "Molecular Basis of Co–operativity in Protein Folding. III. Structural Identification of Cooperative Folding Units and Folding Intermediates", *J. Mol. Biol.*, 1992, 227:293–306.

Murphy, Kenneth, P. et al, "Thermodynamics of Structural Stability and Cooperative Folding Behavior in Proteins", *Adv. Protein Chem.*, 1992, 43:313–361.

Murphy, Kenneth P. et al, "Structural Energetics of Peptide Recognition: Angiotensin 11/Antibody Binding", *Proteins: Struc. Func. Genetics*, 1993 15:113–120.

Murphy, Kenneth P. et al, "Entropy in Biological Binding Processes: Estimation of Transnational Entropy Loss", *Proteins: Struc. Func. Genetics*, 1994, 18:63–67.

Rich, Daniel H., "Inhibitors of Cysteine Proteinases", in *Proteinase Inhibitors*, (eds. Barret & Salvesen) (Elsevier Science Publishers, New York, 1986).

Rich, Daniel H. et al, "Mechanism of Inhibition of Pepsin by Pepstatin. Effect of Inhibitor Structure of Dissociation Constant and Time–Dependent Inhibition", *Biochem. Pharmacol.*, 1980 29:2205–2212.

Roberts, Noel A., "Drug–Resistance Patterns of Saquinavir and Other HIV Proteinase Inhibitors" *AIDS*, 1995, 9:s27–s32.

Schinazi, Raymond F. et al, "Mutations in Retroviral Genes Associated with Drug Resistance", *Int. Antiviral News*, 1996, 4:95–100.

Smith, Ross et al, "Ionization States of the Catalytic Residues in HIV–1 Protease", *Nature Struc. Biol.*, 1996, 3:946–950.

Spinelli S. et al, "The Three–Dimensional Structure of the Aspartyl Protease from the HIV–1 Isolate BRU", *Biochimie*, 1991, 73:1391–1396.

Straume, Martin et al, "Thermodynamic Strategies for Protein Design: Increased Temperature Stability", In *Biocatalysis at Extreme Temperature: Enzyme Near and Above 100°C*, (Adams M.W.W. & Kelly R.M., eds) 1992, pp. 122–135, ACS Books, Washington, DC.

Thaisrivongs, Suvit et al, "Structure–Based Design of Novel HIV Protease Inhibitors: Carboxamide–Containing 4–Hydroxycoumarins and 4–Hydroxy–2–pyrones as Potent Nonpeptidic Inhibitors", *J. Med. Chem.*, 1995, 38:3624–3637.

Thompson, Scott K. et al, "Rational Design, Synthesis, and Crystallographic Analysis of a Hydroxethylene–Based HIV–1 Protease Inhibitor Containing a Heterocyclic $P_2$–$P_2$ Amide Bond Isotere", *J. Med. Chem.*, 1994, 37:3100–3107.

Tisdale, Margaret, "HIV Protease Inhibitors–Resistance Issues", *Int. Antiviral News*, 1996, 4:41–43.

Wang, Yun–Xing et al, "Solution NMR Evidence That the HIV–1 Protease Catalytic Aspartyl Groups Have Different Ionization States in the Complex Formed with the Asymmetric Drug KNI–272", *Biochemistry*, 1996, 35:9945–9950.

Williams, Jeffrey W. et al, "The Kinetics of Reversible Tight–Binding Inhibition", *Methods Enzymol.*, 1970, 19:436–467.

Wlodawer, Alexander et al, "Structure–Based Inhibitors of HIV–1 Protease", *Ann. Rev. Biochem.*, 1993, 179:543–585.

Xie, Dong et al, "Molecular Basis of Cooperativity in Protein Folding V. Thermodynamic and Structural Conditions for the Stabilization of Compact Denatured States", *Proteins: Struct. Func. Genetics*, 1994(a) 19:291–301.

Xie, Dong et al, "Structure Based Prediction of Protein Folding Intermediates", *J. Mol. Biol.*, 1994(b), 24:62–80.

Whitaker, "Protease of Endothia parasitica" Methods in Enzymol. 19:436–445, 1970.

Wiseman et al., "Rapid Measurement of Binding Constants and Heats of Binding Using a New Titration Calorimeter" Anal. Biochem. 179:131–135, 1989.

Experimental Binding Site
showing substrate in white

SB203386

SB203238

SB206343

U100313

U-89360

A-98881

CGP 53820

METHOD FOR PREDICTION OF BINDING TARGETS AND THE DESIGN OF LIGANDS

CROSS-REFERENCE TO RELATED APPLICATION

This application is a divisional of U.S. Application Ser. No. 09/089,097 filed Jun. 2, 1998 now U.S. Pat. No. 6,226,603 claims benefit to U.S. Provisional Patent Application No. 60/066,495, filed Nov. 24, 1997, and claims the benefit of Provisional application Ser. No. 60/048,274, filed Jun. 2, 1997.

STATEMENT AS TO FEDERALLY SPONSORED RESEARCH

This invention was made in part with government support under NIH grant numbers RR04328 and GM51362. The United States government may have certain rights in the invention.

BACKGROUND

1. Technical Field

This invention relates to computer assisted methods for identifying target binding sites on a molecule of interest and methods for designing ligands which bind to a molecule of interest.

2. Background Information

Structure-based drug design is a major activity in pharmaceutical laboratories. The recent development of HIV-1 protease inhibitors is a major testimony to that effect. In structure-based drug design, the overall goal is to design a small molecule that binds to a specific site in a target molecule, usually a protein or other macromolecule. Where the target protein is an enzyme, the specific target site is often the substrate binding site or active site of the enzyme. Where the target protein is a receptor, the specific target site is often the binding site for a natural ligand of the receptor. In all cases the goal is to alter the behavior of the target molecule in a predetermined way as a result of the binding of the small molecule.

The starting point in the design process is the availability of the high resolution structure of the target protein. As noted above, in most situations, the target site for binding of the small molecule drug is the substrate binding or active site of an enzyme or the ligand binding site of a receptor. In some cases the location of these sites on the surface of the target protein is known from biochemical or structural studies. For this reason, most lead compounds are analogues of natural ligands or substrates. The situation is more complicated if the location of these sites is not known or if targeting a second binding site is required (a situation necessary, e.g., in cases where resistance towards an existing drug develops). Furthermore, the optimization of lead compounds is a very demanding endeavor requiring the chemical synthesis and characterization of a very large number of derivatives. It is evident that the availability of an algorithm that can identify, map, and rank binding sites and design ligands would have a positive impact in drug design. The present invention provides such capabilities.

SUMMARY

The invention features a computer-based method for the identification of binding targets in proteins and other macromolecules. More particularly, the invention includes an algorithm aimed at predicting binding targets in proteins and other macromolecules. The algorithm, referred to as "Woolford", requires knowledge of the three-dimensional structure of the selected target protein or target macromolecule.

However, Woolford does not require knowledge of the location or identity of natural binding sites or ligands. Binding targets in the protein are identified and classified according to their expected optimal affinities. Binding targets can be located at the protein surface or at internal surfaces that become exposed as a result of partial unfolding, conformational changes, subunit dissociation, or other events. The entire protein is mapped according to the binding potential of its constituent atoms. In another aspect of the invention, once binding targets are identified, optimal ligands are designed and progressively built by the addition of individual atoms or amino acids in the csae of peptide design that complement structurally and energetically the selected target site.

The Woolford algorithm and the associated methods of the invention are expected to have significant applications in structure-based drug design since they allow: 1) identification of binding targets in proteins and other macromolecules; 2) identification of additional binding targets if a primary binding target is known; 3) design of molecules ("ligand") with optimal binding affinities for the selected binding target; and 4) refinement of lead compounds by defining the location and nature of chemical groups for optimal binding affinity.

The invention features methods for the identification of binding targets in proteins and other macromolecules. Binding targets can be located at the protein surface or at internal surfaces that become exposed as a result of partial unfolding, conformational changes, subunit dissociation, or other events.

The method for the identification of internal binding targets includes the identification of the most probable partially folded conformations of a protein and/or the dissociation energetics.

The invention also features methods for the design of synthetic organic ligands and peptide ligands which bind identified binding targets.

The invention also features methods for optimization of the conformation of ligands and the calculation of the expected binding affinities of ligands.

The invention also features methods for calculating the Gibbs free energy of binding of a ligand to a macromolecule. The method entails the steps of: (a) inputting into the programmed computer, through an input device, data which includes the three-dimensional coordinates and identity of each of the atoms in the ligand, the three-dimensional coordinates and identity of each of the atoms in the macromolecule, and the three-dimensional coordinates of each of the atoms in the complex of the ligand bound to the macromolecule; (b) determining, using the processor, the difference between the Gibbs free energy of the complex of the ligand and the macromolecule and the Gibbs free energy of the uncomplexed ligand and the uncomplexed macromolecule; (c) outputting to the output device the difference between the Gibbs free energy of the complex of the ligand and the macromolecule and the Gibbs free energy of the uncomplexed ligand and the uncomplexed macromolecule.

DETAILED DESCRIPTION

Throughout this description, the preferred embodiment and examples shown should be considered as exemplars, rather than as limitations of the present invention. In the description of this invention, the discussion is centered around proteins but the concepts are equally valid for other molecules.

1. Overview of the Woolford Algorithm

A protein molecule has the potential to define many binding sites (binding targets). The vast majority of those binding targets, however, are expected to bind ligands with extremely low affinities. Also, because most of those binding targets are not topologically or structurally unique, they are expected to lack specificity. A case in point is the association of denaturants to proteins, or the association between protein and molecules like ANS that recognize features that are common to nearly all proteins. Only few spots on the surface of a given protein will exhibit the intrinsic characteristics necessary for high affinity binding. These characteristics include chemical, topological and structural features that together are able to maximize energetic contributions to the binding affinity.

In drug design, the binding site is usually defined by the location of the natural active site or the location of the recognition site for a natural ligand. It is normally found experimentally by studying a complex formed by the protein with a natural ligand or substrate. Many approaches to rational drug design involve replacing the natural ligand or substrate by an inert ligand, an inhibitor or some other molecule that alters the natural activity of the target protein. HIV-1 protease inhibitors, for example, inhibit the viral protease by competing with the natural substrates for the same binding site. The situation is far more difficult if the location of the substrate or ligand binding site on the target molecule is not known or if a second site on the target molecule is desired.

In contrast to many conventional approaches to rational drug design, the methods of the invention do not require advance knowledge of the location of the substrate or ligand binding site (target site) on the target molecule. This is because the methods of the invention, through the use of the Woolford algorithm, permit the identification of target sites for drug design on a given target molecule by producing a complete mapping of the optimal binding contributions of each atom of the target molecule. The Woolford algorithm produces a map of the optimal binding contributions of each atom through the use of an idealized ligand that explores the entire surface of the target molecule, usually a protein, and defines the maximal binding contribution of each atom in the target molecule under ideal conditions.

Figure 1:
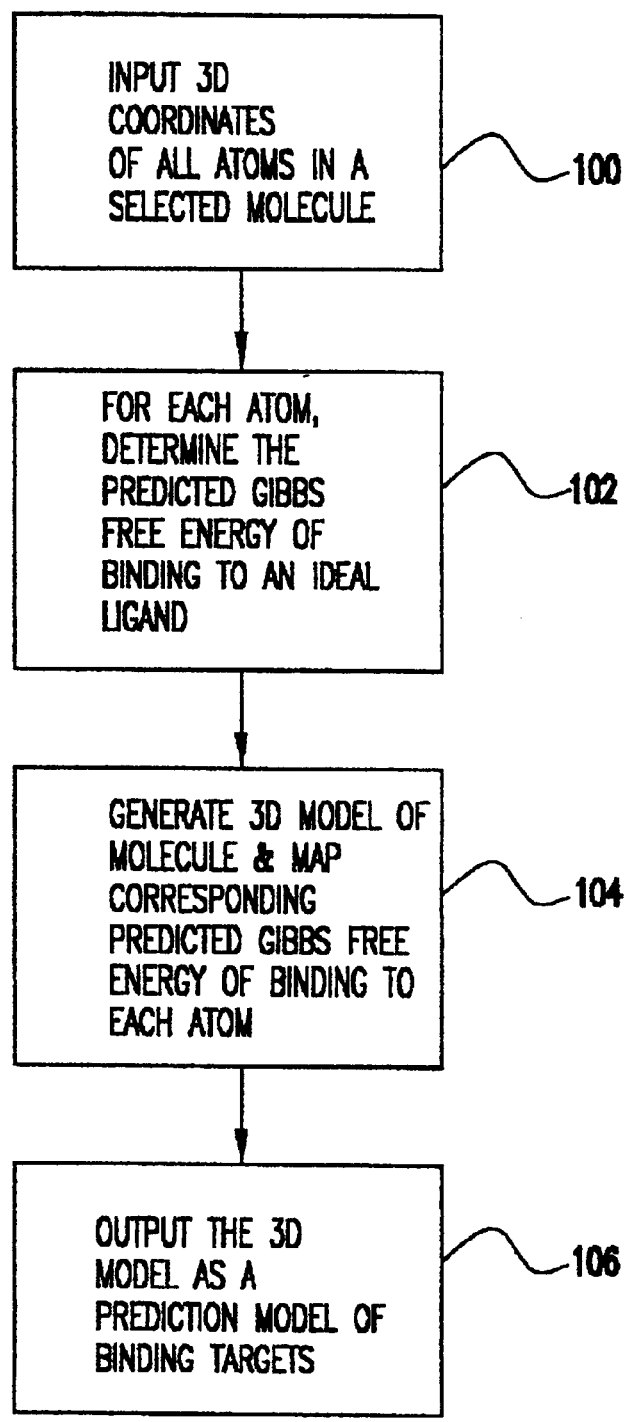
FIG. 1 is a flow chart of the basic Woolford algorithm.

FIG. 1 is a flowchart of the basic Woolford algorithm. Measured three-dimensional coordinates of a selected molecule are input into a computer system (STEP 100). For each atom of the molecule, the computer processor determines a predicted Gibbs free energy of binding of the atom to the ideal ligand for the atom (STEP 102). A three-dimensional prediction model of binding targets in the selected molecule is then generated by the processor using the three-dimensional coordinates of each of the atoms in the selected molecule, and the corresponding predicted Gibbs free energy of binding determined in STEP 102 is mapped onto each atom depicted in the three-dimensional prediction model (STEP 104). Lastly, the three-dimensional prediction model of binding targets is output to a suitable output device as the computed prediction of the actual binding sites of the molecule (STEP 106).

The binding potential of each atom is determined by the Gibbs energy of binding. The optimal contribution of each atom in the protein to the binding energy is computed by using a modification of known structural parameterization, described further below (Bardi et al., 1997; D'Aquino et al., 1996; Freire et al., 1991; Freire, 1993; Gomez et al., 1995(a); Hilser et al., 1996(b); Lee et al., 1994; Luque et al., 1996; Luque et al., 1997; Murphy et al., 1992(a); Murphy et al., 1992(b); Murphy et al., 1993; Murphy et al., 1994; Straume et al., 1992; Xie et al., 1994(a); Xie et al., 1994(b)).

Protein surfaces (either external or internal) are topologically and chemically heterogenous. From a topological point of view, protein surfaces are rough and characterized by the presence of depressions, cavities, crevices, hills, prominences, etc. From a chemical point of view, protein surfaces are heterogenous and characterized by the presence of chemical groups that exhibit different characteristics, e.g., hydrophobic groups, polar groups, groups that are electrically charged positively or negatively, etc. In general, a binding site is a site on the protein that has topological and chemical characteristics that allow another molecule with complementary topological and chemical characteristics to attach to that site with a relatively high affinity.

The Woolford algorithm is capable of identifying and mapping potential target sites on a target molecule (e.g., a protein) including natural active sites, and classifying each site according to its optimal binding affinities. Furthermore, the algorithm creates an ideal ligand that elicits the maximal binding potential of each target site. This ideal ligand can be used as a blueprint for the identification or synthesis of organic molecules that best approximate the characteristics of the ideal ligand.

The Woolford algorithm will be illustrated in a simple way. Any region on a protein is considered to be a potential binding site. Importantly, not every region has the same binding potential. Only very few spots on a protein have the potential for high binding affinity. In fact, the vast majority of potential binding sites will display minimal affinity if the ideal ligand for that site were available. The first goal is then to identify those regions of the protein that have the highest binding potential. This can be illustrated by imagining a hypothetical protein surface with a binding site defined by four different chemical groups. A ligand will bind to that site if it complements the site structurally and chemically so that the interaction is energetically favorable. The overall goal in molecular design is precisely the design of a molecule which will be complementary to the groups in the binding site. However, even if a ligand that exhibits high complementary is found, high binding affinity is not guaranteed. There is an upper limit to the binding affinity that can be achieved by any given binding site. This upper limit depends on the chemical composition (atom types), size and topology of the binding site itself, i.e., it is an intrinsic property of the protein. In general, this upper limit will only by achieved by an ideal ligand that offers a perfect match to the site. Not all sites have the same upper limit. In principle, this upper limit can be estimated for an idealized perfect ligand. This upper limit affinity is referred to as the "binding potential." In essence, the binding potential represents the maximal contribution of any given atom or group of atoms within the protein to the Gibbs energy of binding of the best possible ligand.

In proteins there are many chemical groups all of which can serve as potential binding sites, albeit with vastly different binding potentials. The goal of the Woolford algorithm is to estimate the binding potential of each atom in the protein and select the regions that contain a high density of atoms with high binding potentials. These regions constitute binding targets for drug design.

The problem addressed by the algorithm can be expressed succinctly as follows: Given a certain number of groups with different geometries, topologies and chemical characteristics, can we identify and map the region or regions that define high affinity binding sites? Can we rank those binding sites in terms of their binding potentials? Furthermore, can we create the ideal ligands that perfectly complement each binding site? The solution to this problem has significant implications in drug design: 1) it allows identification of binding targets in proteins; 2) it allows identification of additional targets if the primary target is known; 3) it allows refinement of lead compounds by defining the location and nature of chemical groups for optimal binding affinity; and 4) it allows the design of new ligands for each binding site.

The highest affinity that can be achieved by a binding site corresponds to that expected for the ideal ligand. The affinity towards the ideal ligand is by definition the upper limit or optimal affinity that can be expressed by any given atom and is used to define the binding potential. The ideal ligand is by definition perfectly complementary to the binding site. In addition, the conformation of the ideal ligand in solution is equal to the bound conformation and does not lose conformational entropy upon binding. The ideal ligand is a computer construct, the perfect match for a binding site. For this reason, it also provides the model to design and build real ligands.

Each atom in the protein is a potential binding target, however each atom does not have the same binding potential. A protein region with the potential to bind a ligand with high affinity is one that exhibits a high density of atoms with high binding potential. The task of identifying target sites reduces to a large extent to the computation and mapping of the protein according to the binding potential of its different atoms.

2. Overview of the Ligand Design Process

Figure 2:
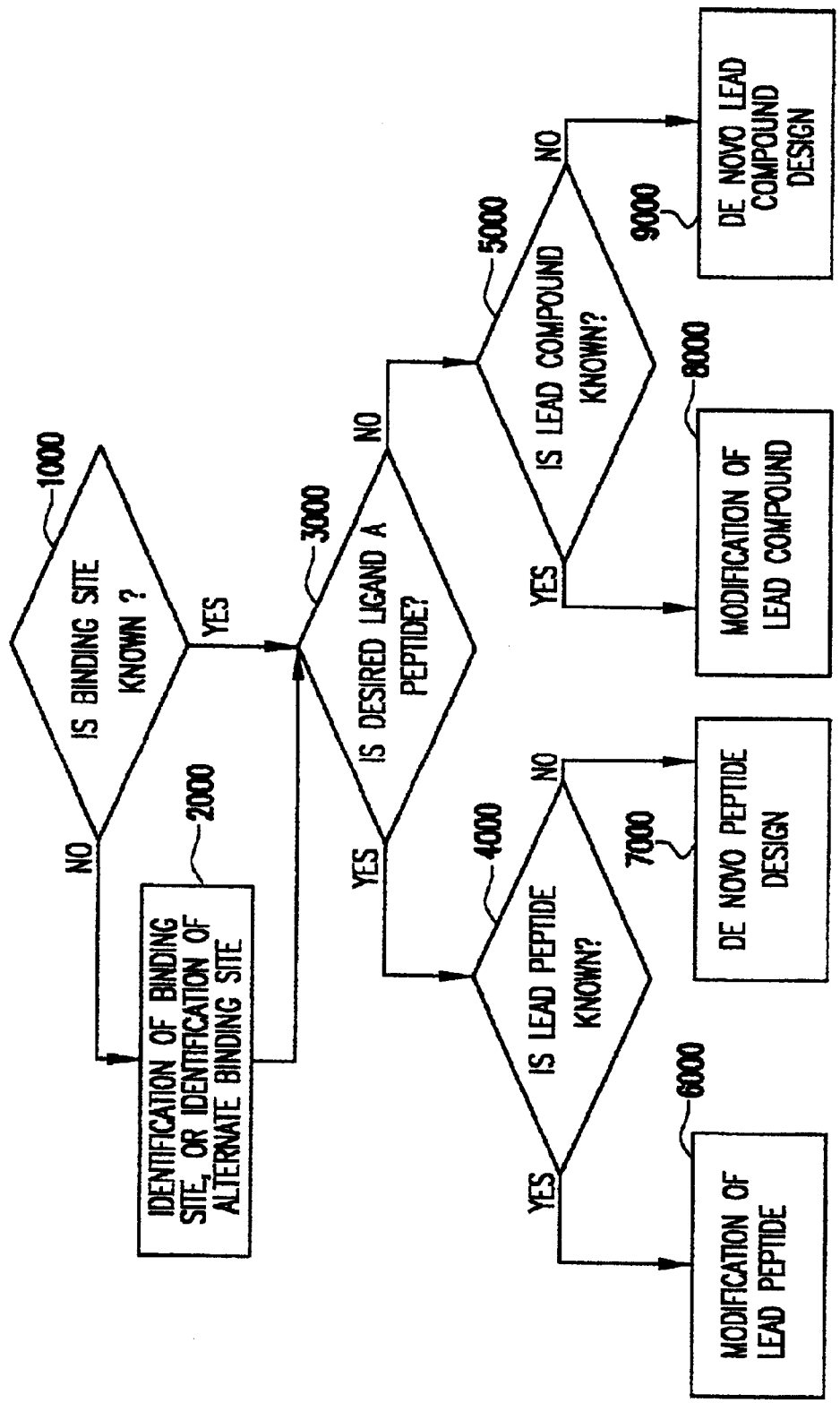
FIG. 2 is a flow chart of the algorithm used for ligand design.

The overall flow of the ligand design process is illustrated in FIG. 2. First, a binding target site is identified (STEP 1000). In some cases the target binding site will be known based on experimental data. In cases where the target binding site is not known, the Woolford algorithm can be used to select a target binding site (STEP 2000). In addition, even where a target binding site is already known, it may be desirable to identify, using the Woolford algorithm, an alternate target binding site (STEP 2000).

Second, the user selects the general structure of the desired ligand (STEP 3000), e.g., either a peptide or some other compound (e.g., a non-peptide organic molecule).

Figure 4:
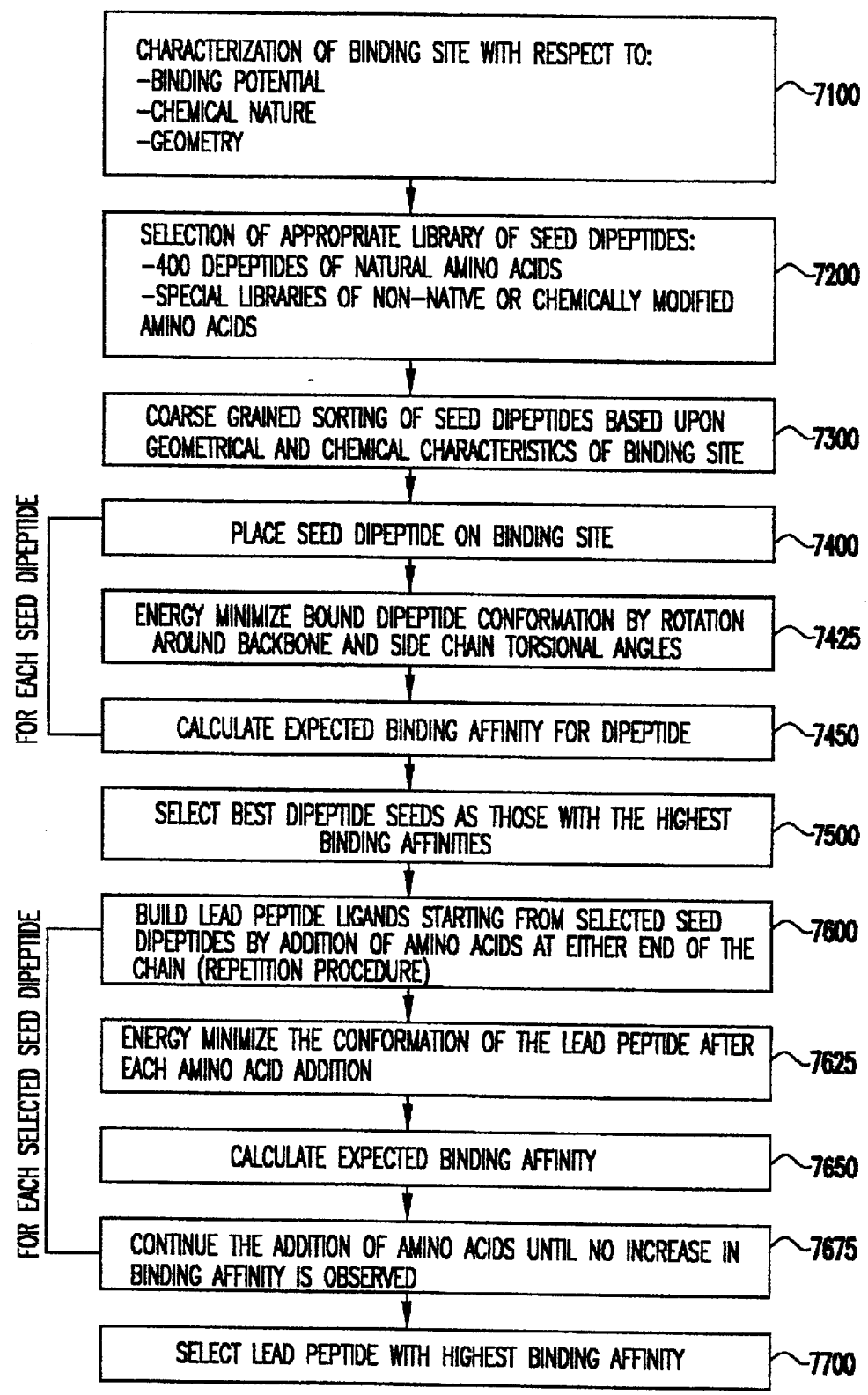
FIG. 4 is a flow chart which details the creation of a lead peptide ligand.
Figure 6:
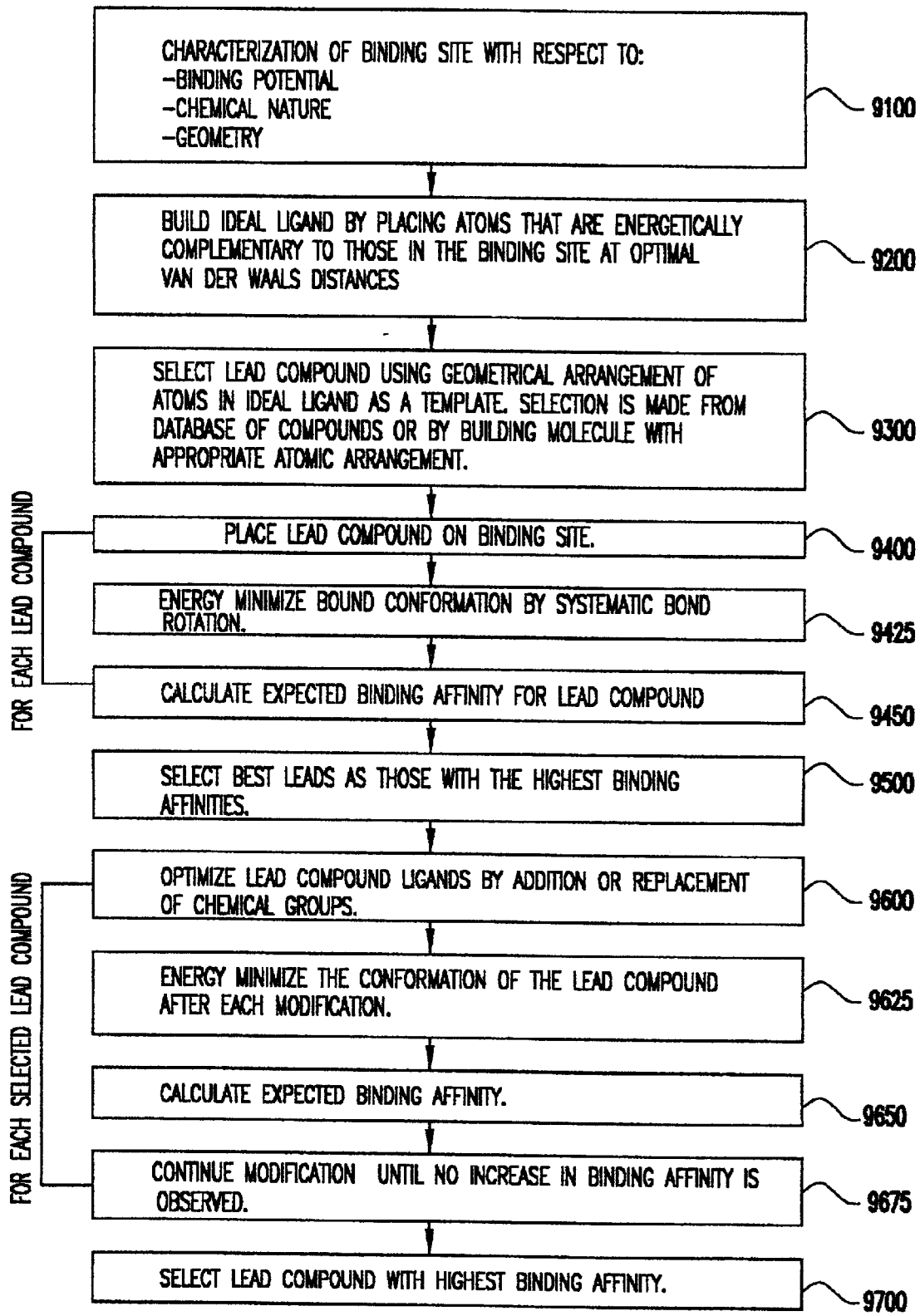
FIG. 6 is a flow chart which details the creation of a lead compound ligand.

Third, a lead ligand (either a peptide (STEP 4000) or some other compound (STEP 5000)) is identified either from experimental data or through ab initio calculations, i.e., calculation of an "idealized lead ligand" (STEP 7000 or STEP 9000), see FIG. 4 and FIG. 6.

Figure 5:
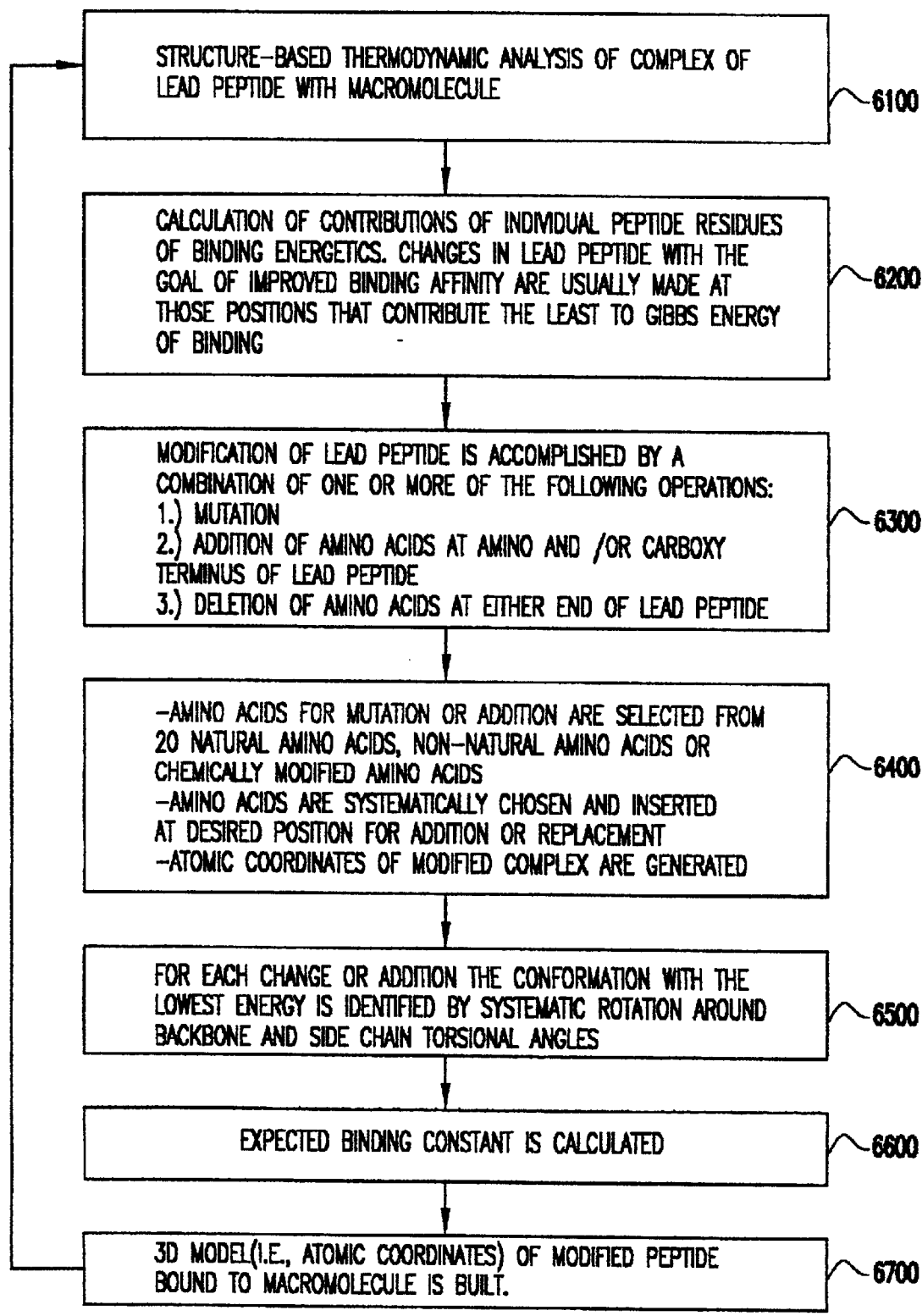
FIG. 5 is a flow chart which details the lead peptide ligand modification procedure used in the ligand design algorithm.

Fourth, the lead ligand is modified in either STEP 6000 or STEP 8000 and the expected binding constant is calculated (see FIG. 5 and FIG. 7) using the structural parameterization described above.

Binding Site Identification

Figure 3:
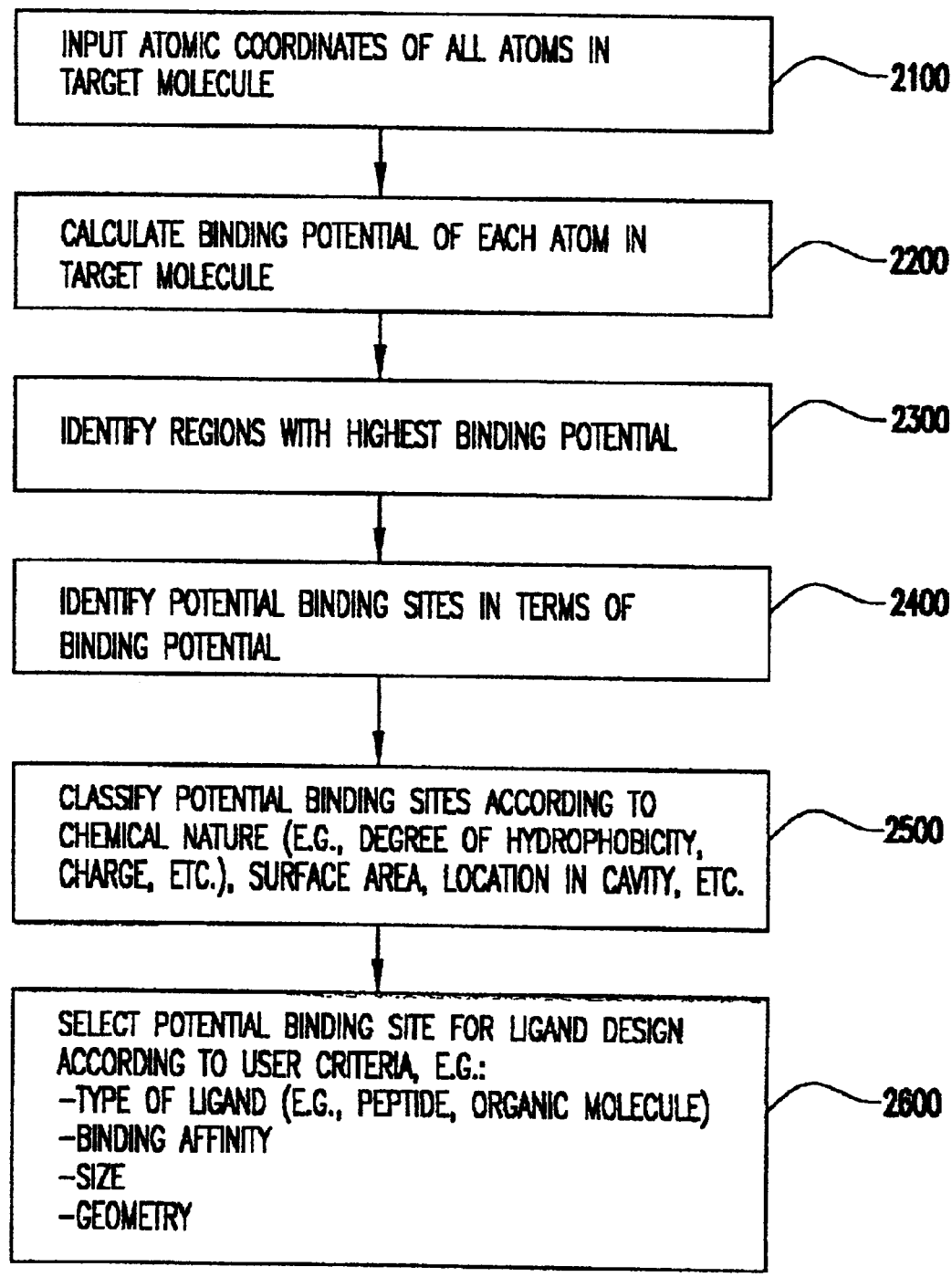
FIG. 3 is a flow chart which details the binding site identification procedure used in the ligand design algorithm.

The first step in the ligand design process is outlined in FIG. 3 which is a flow chart of the Woolford algorithm used to identify potential target binding sites. Measured three-dimensional coordinates of a selected target molecule are input into a computer system (STEP 2100). For each atom of the target molecule, the computer processor determines a predicted Gibbs free energy of binding of the atom to the ideal ligand for that atom. A three-dimensional model of binding targets in the selected target molecule is then generated by the processor using the three-dimensional coordinates of each of the atoms in the selected target molecule. The corresponding predicted Gibbs free energy of binding is then mapped onto each atom depicted in the three-dimensional model of the target molecule (STEP 2200). The processor identifies regions with the highest binding potential (STEP 2300 and STEP 2400) and classifies each potential binding site according to chemical nature, surface area, location, etc (STEP 2500). Lastly, the processor selects a potential target binding site according to user criteria, e.g., type of ligand, binding affinity, size, geometry, and a three-dimensional prediction model of the binding target is output to a suitable output device (STEP 2600).

De Novo Design of a Lead Peptide Ligand and Modification Thereof

FIG. 4 is a flow chart of the process used for the de novo design of a lead peptide design. Once the target binding site is selected, the processor characterizes the binding site according to one or more criteria, e.g., its geometry, chemical nature, and binding potential (STEP 7100). With this information, the processor selects several "seed" dipeptides from a library consisting of 400 natural occurring dipeptides, non-native amino acids, and chemically modified amino acids (STEP 7200).

The processor then sorts through the possible seed dipeptides and determines which seed dipeptides might make suitable ligands given their geometry and chemical characteristics (STEP 7300). The binding affinity for each of the selected seed dipeptides is calculated as follows. First, the processor places the seed dipeptide onto the selected target binding site (STEP 7400). Second, the processor minimizes the energy function of the bound seed dipeptide through rotation around the peptide backbone and side chain torsional angles (STEP 7425). Third, the processor calculates the binding affinity for the seed dipeptide when the seed dipeptide is in the energy minimized conformation determined in the preceding step (STEP 7450).

After this process has been completed, the processor selects the seed dipeptide ligands with the highest binding affinities (STEP 7500).

The processor now begins a "reptation" procedure, described below, which builds a lead peptide ligand from a selected seed dipeptide by adding amino acids on one or both ends of the selected seed dipeptide (STEP 7600). After each amino acid addition the processor minimizes the energy function of the bound lead peptide through conformational changes in the backbone rotation and side chain torsional angles (STEP 7625). Once minimized the processor calculates the binding affinity for the lead peptide (STEP 7650).

The processor continues, in STEP 7675, to add amino acids (STEP 7600), minimize the conformational energy (STEP 7625), and calculate the binding affinity (STEP 7650) until the calculated binding affinity does not increase.

The processor selects the next seed dipeptide and begins to build another lead peptide in the same manner as described above (STEP 7500 through STEP 7675). Once the processor has used all of the seed dipeptides to build lead peptides, the lead peptide with the highest binding affinity is identified (STEP 7700). This lead peptide can be subjected to modification, as described below (see FIG. 5).

Once a lead peptide ligand has been identified, it can be modified. This process is outlined in FIG. 5 which is a flow chart of a modification procedure for an identified lead peptide ligand.

First, the computer processor calculates the Gibbs free energy of binding of the lead peptide to the target binding site (STEP 6100). The processor then calculates the contribution of each amino acid residue to the binding energy (STEP 6200). The amino acid residues which contribute the least to the binding energy are selected for modification by amino acid mutation, addition, or deletion (STEP 6300).

The processor systematically selects and inserts amino acids used for addition and mutation to create and altered lead peptide (STEP 6400). The processor generates the atomic coordinates for each altered lead peptide (STEP 6400). The lowest conformational energy of each altered lead peptide is then determined (STEP 6500).

Next, the expected binding constant for binding of the altered lead peptide to the target binding site is calculated (STEP 6600). A three-dimensional map of each altered lead peptide bound to the target binding site is then determined (STEP 6700). The modification procedure (STEP 6100 through STEP 6700) can be repeated as necessary until modification of the lead peptide ligand results in an improvement of the calculated binding affinity.

De Novo Design of a Lead Compound Ligand and Modification Thereof

FIG. 6 is a flow chart of an algorithm used to create a lead compound ligand. Once the target binding site is identified based either on experimental data or the algorithm presented above (see FIG. 3), the processor characterizes the binding site according to its geometry, chemical nature, and binding potential (STEP 9100). With this information, the processor places, at optimal van der Waals distances, several atoms that are energetically complementary to the atoms in the binding site (STEP 9200). The geometrical arrangement of the ensemble of atoms is used as a template to select several lead compounds (STEP 9300). The selection is made either from a database of known compounds or by building a molecule with an appropriate atomic arrangement.

The binding affinity for each lead compound is calculated as follows. First, the processor places one of the lead compounds onto the selected target binding site (STEP 9400). Second, the processor minimizes the energy function of the bound lead compound by systematic bond rotation (STEP 9425). Third, the processor calculates the binding affinity for the lead compound in its energy minimized configuration (STEP 9450). The processor then selects the lead compounds with the highest binding affinities (STEP 9500).

The processor now begins a procedure—similar to the reptation procedure discussed above—to optimize each of the selected lead compounds through addition or replacement of chemical groups (STEP 9600). After each addition or replacement, the processor minimizes the energy function of the bound modified lead compound through systematic bond rotation (STEP 9625). Once the energy minimized conformation of the modified lead compound is identified, the processor calculates the binding affinity of the energy minimized, modified lead compound for the target binding site (STEP 9650). The processor, in STEP 9675, continues to modify (STEP 9600), minimize the conformational energy (STEP 9625), and calculate the binding affinity (STEP 9650) until the calculated binding affinity does not increase. The processor selects the next lead compound and begins to modify the lead compound in the same manner as described above (STEP 9500 through STEP 9675). Once the processor has modified all of the lead compounds, the lead compound with the highest binding affinity is selected (STEP 9700) to undergo further modification (see FIG. 7).

Figure 7:
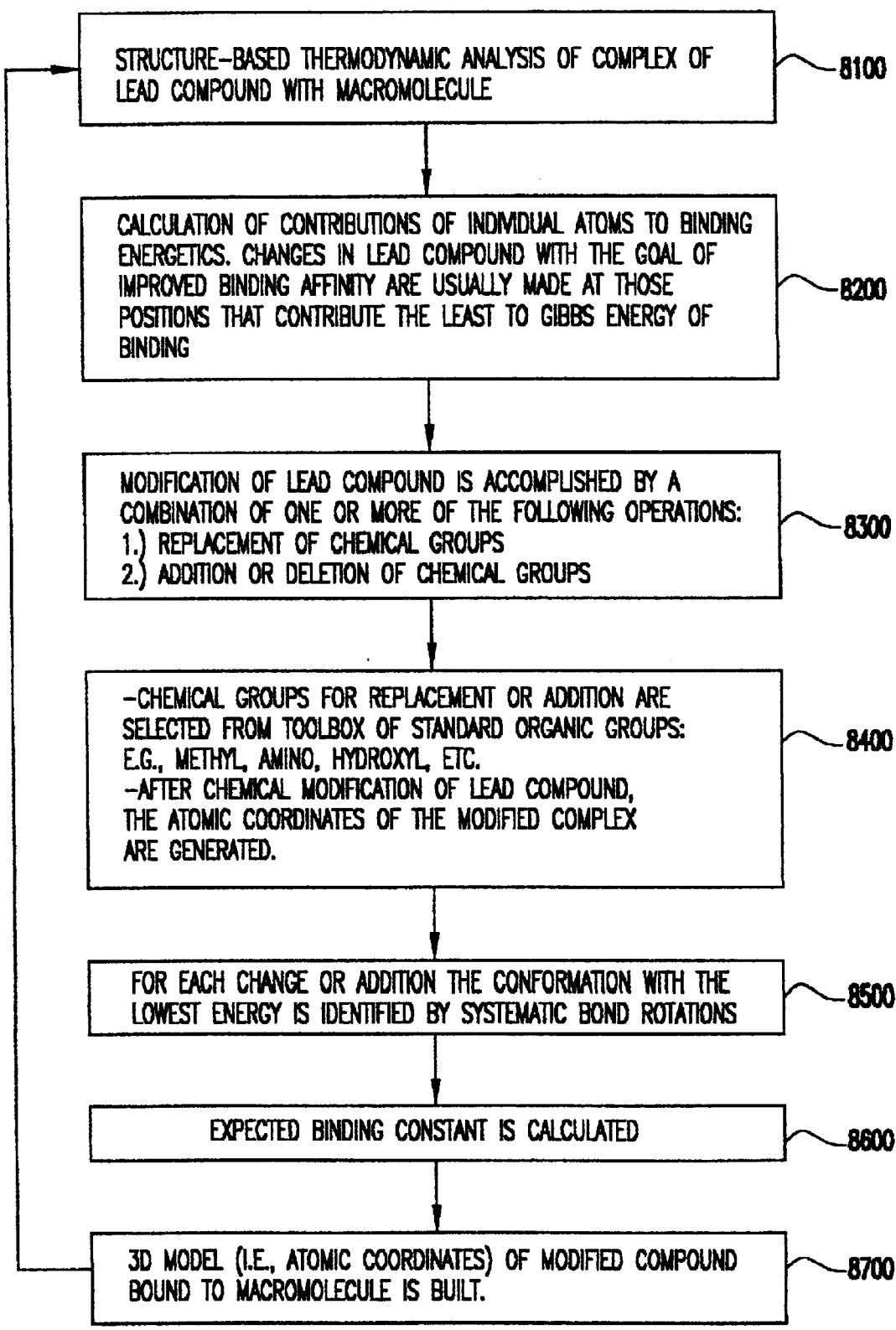
FIG. 7 is a flow chart which details the lead compound ligand modification procedure used in the ligand design algorithm.

FIG. 7 is a flow chart of a modification procedure for a lead compound ligand. The computer processor calculates the Gibbs free energy change of the lead compound bound to the target molecule binding site (STEP 8100), and identifies the contribution of each atom to the binding energy (STEP 8200). The atoms which contribute the least to the binding energy are selected for modification by replacement of chemical groups, addition of chemical groups, or deletion of chemical groups (STEP 8300). The chemical groups for replacement or addition are selected from a toolbox of standard organic groups, e.g., methyl, amino, hydroxyl, and the like (STEP 8400). For each modification, the processor generates the atomic coordinates of the modified lead compound (STEP 8400), the lowest energy conformation of the modified lead compound (STEP 8500), and the expected binding constant for each energy minimized, modified lead compound (STEP 8600). A three-dimensional map is generated for the mutated compound bound to the target binding site (STEP 8700). The modification procedure (STEP 8100 through STEP 8700) can be repeated as necessary until modification of the lead compound ligand results in an improvement of the calculated binding affinity.

3. Calculation of Binding Potential per Atom

The binding affinity is determined by the Gibbs energy of binding. The binding affinity of the ideal ligand is calculated by computing the expected Gibbs energy of each atom in the protein for an ideal ligand. The Gibbs energy is context sensitive and depends on the position and nature of the remaining atoms. The binding potential is calculated from structure-based thermodynamic considerations. In the energy computations presented here, a structural parameterization of the energetics described herein is used. The previously known level of refinement of this parameterization is summarized in the following references: (Bardi et al., 1997; D'Aquino et al., 1996; Gomez et al., 1995(a); Gomez et al., 1995(b); Hilser et al., 1996(b); Luque et al., 1996). This structural parameterization of the energetics has been shown to correctly predict binding affinities from structure for a variety of molecules, including the set of HIV-1 protease inhibitors for which high resolution structures are available (Example 1). The Woolford algorithm, however, is not dependent on this energy function and can be implemented with other energy functions. The implementation of the Woolford algorithm with any other energy function is within the scope of the present invention.

The Gibbs energy of binding is composed of enthalpic and entropic components. Both components include contributions due to the formation of interactions between ligand and protein, and contributions due to changes in hydration. The enthalpic contributions are a function of the separation distance between atoms and the changes in atomic accessibility to the solvent. The entropy change contain solvent contributions which are also proportional to changes in solvent accessibility, and the reduction in conformational degrees of freedom. Changes in translational degrees of freedom are the same for different ligands and therefore do not contribute to discrimination between binding affinities even though they contribute to the actual affinity.

If the ideal ligand is assumed to establish the average atomic packing characteristics found in the interior of proteins, then the major contribution to the enthalpy value at any given temperature ($\Delta H_{gen}(T)$) is given by an equation of the form:

$$\Delta H_{gen}(T) = a_H(T) \cdot \Delta\Delta SA_{ap} + b_H(T) \cdot \Delta\Delta SA_{pol}$$

where the coefficients $a_H(T)$ and $b_H(T)$ are structural parameterization parameters and $\Delta\Delta SA_{ap}$ and $\Delta\Delta SA_{pol}$ are the changes in apolar and polar solvent accessibilities for the atoms in both protein and ligand upon binding. Similarly, at any given temperature T, the solvent related entropy $\Delta S_{solv}(T)$:

$$\Delta S_{solv}(T) = a_S(T) \cdot \Delta\Delta SA_{ap} + b_S(T) \cdot \Delta\Delta SA_{pol}$$

also scales in terms of the changes in apolar and polar solvent accessibilities with a set of coefficients $a_S(T)$ and $b_S(T)$ also obtained form the known structural parameterization of the energetics. Changes in conformational entropy on the other hand are not linearly related to changes in accessibility even though the conformational flexibility is expected to be proportional to the exposure to solvent. Electrostatic interactions are calculated according to a standard coulombic potential that depends on the interatomic distances between charges.

It is clear from the equations above that the surface area that becomes buried from the solvent upon binding, expressed as changes in solvent accessibilities, are key quantities in the calculation of binding potentials, especially since their magnitude depends on the topological configuration of the binding site. For any atom in the protein or ligand, the change in solvent accessibility is equal to the accessibility in the free form minus the accessibility of the same atom in the complex. The atomic accessibility in the free protein is computed from the high resolution structure. The change in solvent accessibility upon binding depends on the topological location of the atom and the size and geometry of the ligand.

The fraction of area buried from the solvent upon binding of a small molecular weight ligand depends on the geometry of the surface. In general, the change in solvent accessible surface area upon binding is a function of the concavity of the surface in which it is located. In general, except for charged groups, the binding energetics is proportional to the change in solvent accessibility (i.e., the amount of surface area that becomes buried from the solvent upon binding). This is why high affinity binding sites are generally located in pockets or crevices that optimize the amount of surface that is buried from the solvent.

4. Identification and Classification of Binding Targets

Binding targets are identified by mapping the binding potential of each atom on the three-dimensional structure of the protein. Binding targets can be classified according to their chemical nature (e.g., degree of hydrophobicity, charge, etc.), their surface area or other appropriate parameter. In most situations the size of the binding target and hydrophobicity are the most important parameters. Since small molecular weight compounds are preferred as pharmaceutical drugs, high affinity must be elicited in a small binding target. This consideration strongly favors highly hydrophobic ligands, making the hydrophobic effect the dominant driving force in the binding of these small organic molecules.

The Woolford algorithm allows the user to examine binding potentials in terms of the degree of hydrophobicity of the site. So, for example, it is possible to search for the binding targets with the highest binding potential, or for the binding targets with the highest potential for a given degree of hydrophobicity. Within this context, the degree of hydrophobicity is expressed in terms of the proportion of polar and non-polar atoms at any given site. The surface area of integration (the size of the binding site) is also a variable that can be set by the user.

5. The Ideal Ligand

Once a potential binding site is identified, the ideal ligand is built by placing atoms that are energetically complementary to those in the binding site at optimal van der Waals distances. The basic building set is composed of carbon, nitrogen, and oxygen atoms even though other atom types can be included. Atoms from this pool are used to fill the binding site. The number, type and exact location of each atom is obtained by global optimization of the binding Gibbs energy.

The resulting set of atoms (number, type and position coordinates) define the ideal ligand. At this stage, the atoms in the ideal ligand do not belong to any particular type or class of molecule. At this level, the ligand is defined as an aggregate of atoms that satisfy only van der Waals radii requirements and optimal energy placements. The particular way in which the ligand atoms are bonded to each other is solved later using appropriate organic chemistry procedures.

Different atom types are placed in three dimensional space such that the binding affinity towards the selected target is optimal. The atoms in the ideal ligand are not bonded together. They define a three-dimensional blueprint for the identification and/or design of organic molecules that closely approximate the characteristics of the ideal ligand.

6. Ligand Building

The ideal ligand is defined as a three-dimensional array of atoms which will maximize the binding affinity if they were forming a single molecule. As such, this array can be used as a blueprint to identify or construct a molecule that will present the same atomic arrangement to the binding target. This arrangement can be defined solely by the atoms specified by the algorithm or by a larger number of atoms, or as required to present the appropriate binding surface to the target.

The binding affinity of a real ligand can only approximate that of the ideal ligand. The ideal ligand not only exhibits perfect complementarity but also lacks conformational degrees of freedom when free in solution, i.e., it does not lose conformational entropy upon binding. These requirements are very difficult to reproduce in reality.

The process of building a ligand molecule involves the identification of the best bonding arrangement consistent with the positions coordinates of the atoms in the ligand molecule. This can be done by using graph theory considerations or other appropriate procedures including identification of the most appropiate ligand molecule from an empirical database of chemical compounds. This process does not always lead to a unique molecule and in some situations several potential candidates are possible.

7. Non-surface Binding Targets

In the description of the invention the protein surface of the native protein structure has been used as an example to identify binding targets. The algorithm, however, also applies to internal protein surfaces that become exposed as a result of conformational changes, or to oligomerization interfaces in multimeric proteins. Also, the application of this algorithm to other macromolecules (e.g., nucleic acids) or biological membranes should also be included in the invention.

Traditionally, the location of binding targets has been restricted to the exposed surfaces of a protein. A new and still unexplored area is the targeting of ligands to internal surfaces. The Woolford algorithm also considers the existence of binding sites located at internal surfaces. These internal surfaces are normally not accessible to the solvent or ligands. They are located at interfaces between different protein regions or at the interfaces between subunits in the case of multisubunit proteins. In order for binding to occur, part of the protein needs to unfold (or separate through a conformational change from the rest of the protein) and make the binding site available. Formally, it can be said that the ligand stabilizes a partially folded state of the protein, i.e., a protein state in which some regions are folded and other regions are unfolded.

In the above situation, the total Gibbs energy associated with the binding of the ligand is the sum of the Gibbs energy required to unfold the region of the protein that exposes the binding site (or the Gibbs energy for the conformation change) plus the intrinsic Gibbs energy of binding.

It is evident that the total binding energy will be optimized if the Gibbs energy required to unfold the region of the protein that exposes the binding site is small. Therefore, one crucial element in the discovery of internal binding sites is the correct identification of those regions of the protein that have the lowest structural stability; or, equivalently, the identification of the partially folded states that have the highest probabilities of being populated.

The algorithm for identifying the most probable partially folded states involves the use of the high resolution structure of a protein as a template to generate a large number of partially folded conformations. Partially folded conformations are created by unfolding certain regions of the protein with the computer, while maintaining the remaining regions in their native conformation. The Gibbs energies of all the partially folded states are calculated using the structural parameterization of the energetics in conjunctions with a set of structural parameters optimized for the unfolded state. The partially folded state with the highest probability is the one with the lowest Gibbs energy.

The generation of partially folded states is achieved by using a combinatorial algorithm followed by refinement of the resulting partially folded structure. The combinatorial algorithm considers the protein as being formed by an arbitrary number of folding units. Each folding unit can be either folded or unfolded. Protein states are generated with the computer in a combinatorial way by folding and unfolding the folding units in all possible combinations. The total number of states that is generated is proportional to the number of folding units (N) and is equal to $2^N$. The number of folding units determines the resolution of the analysis. The starting point is usually N=16 which results in an initial ensemble of 65536 states. Once the partially folded state with the lowest Gibbs energy is identified, the precise amino acid boundaries are located by using a refinement procedure which involves moving the boundaries between folding/unfolding regions by one residue at a time.

Once the most probably partially folded state is found, the surface that becomes exposed as a result of the partial unfolding is identified. This surface is located in the folded regions of the partially folded state but is buried from the solvent in the native state. This surface becomes exposed to the solvent upon unfolding of the adjacent regions. The identification of the binding target with the highest binding potential on this surface follows the same procedure described in this disclosure for other binding targets.

8. Design of Peptide Ligands

An algorithm for the design and docking of peptide ligands is presented. This algorithm uses the three-dimensional structure of a protein or other macromolecule as a template for the design of peptides that will associate with pre-defined binding affinity to selected target sites in a protein molecule. Two situations are considered, one in which the high resolution structure of the target protein in association with a lead or wild-type peptide is known; and one in which only the structure of the target protein is known. In the first situation, ligand design can be done by adding, deleting or replacing specific amino acids at specific locations within the lead peptide. In the second situation, the starting point in the design process is the definition of a minimal core peptide which is treated as a virtual lead peptide by the algorithm. Molecular design is implemented by sequential molecular or atomic replacement, addition or deletion followed by energy minimization. Molecular construction is performed by implementing an energy-guided "reptation" procedure. The minimal core peptide is defined by a systematic or exhaustive search of a library of small peptides (dipeptides, tripeptides, etc.) until an appropriate lead peptide is found. In all energy procedures, an empirically derived structural parameterization of the energetics is used. The algorithm can be used with known target sites or to discover new peptide target binding sites. Also, the algorithm is implemented for natural or non-natural amino acids.

Studies with different peptides that bind to proteins (e.g. angiotensin, pepstatin A, etc.) indicate that the total binding energy is not evenly distributed throughout the molecule and that some groups (often called hot-spots in the literature) carry a larger proportion of the binding energy. By using small peptides as probes, it is possible to identify specific sites in the protein that have the highest potential binding affinity. This is a computationally tractable problem. If only natural amino acids are included, 400 dipeptides and 8,000 tripeptides are possible. The numbers do not increase significantly if non-natural amino acids are included. The first step in the procedure is the mapping of the protein surface in terms of the binding potential of each of its constituent atoms. Using this map, the peptides that are complementary to the sites with the highest binding potential are selected. At the end of this procedure, a map of the protein surface in terms of maximal binding affinities for small lead peptides is obtained. This map is then used in the selection of a binding site and the design of a peptide ligand using the lead peptide as the starting point.

In the past, one of the main obstacles to structure-based molecular design algorithms has been the absence of an energy function with the capability to accurately predict the binding affinity. The present invention provides an energy function which can accurately predict the binding affinity.

As noted above, the binding affinity is determined by the Gibbs energy of binding. The optimal contribution of each atom in the protein to the binding energy is computed by using a special modification of a previously developed structural parameterization of the binding energetics (Bardi et al., 1977; D'Aquino et al., 1996; Freire et al., 1991; Freire, 1993; Gomez et al., 1995(a); Hilser et al., 1996(b); Lee et al., 1994; Luque et al., 1996; Luque et al., 1997; Murphy et al., 1992(a); Murphy et al., 1992(b); Murphy et al., 1993; Murphy et al., 1994; Straume et al., 1992; Xie et al., 1994(a); Xie et al., 1994(b)).

9. Binding Sites and Identification of a Lead Peptide

In the preferred embodiment, the design of a peptide ligand begins with the identification of a lead peptide. There are four possibilities, all of which can be addressed by the algorithm:

1) The lead peptide and the binding site are not known.
2) The binding site is known but the lead peptide is not known.
3) The lead peptide is known and the binding site is not known.
4) The lead peptide and the binding site are known.

In the first case, the first task is to use the high resolution structure of the protein in order to identify the location of the binding site and the amino acid sequence of the lead peptide (usually but not limited to a dipeptide). This is a joint search since the expected binding potential of a given site in the protein cannot be realized unless the optimal peptide sequence is specified. The identification of candidates for possible locations of the binding site is done by constructing a map of the protein surface in terms of potential binding affinities for "idealized lead peptides". Once the best candidates have been identified, a systematic search with the full atomic structures of the peptides is made. This procedure results in the selection of a binding site and corresponding lead peptide, which constitutes the starting point for the design of the final peptide ligand.

In the second case, the location of the binding site is known and therefore the search for the best location and sequence of the lead peptide is restricted to a smaller region of the protein. In this case, the identification of the best lead peptide is made directly with full atomic structures of all possible lead peptides.

In the third case, the ligand peptide is known but the binding site is not known. This situation approaches the classical docking problem. In our algorithm, the original ligand peptide is decomposed into its elementary dipeptide components. Then, the same procedure used in case one is performed for each of the elementary dipeptides. Elementary dipeptides are used in the analysis because their conformations are computer tractable while those of longer peptides are not. Once the lead peptide is identified, the same energy minimization procedure is used except that the rest of the peptide sequence is already known.

In the fourth case, where the lead peptide and the binding site are known, the problem can reduce to finding the conformation that minimizes the binding energy. However, in situations in which the high resolution structure of a protein in complex with a peptide ligand is known, the goal is often the design of a different version of the peptide with different binding characteristics. If this is the case, the experimental peptide is used as the lead peptide. Here, the first task is to map the relative contributions of each amino acid in the peptide to the binding energy. This energy map is then used to select amino acids that are targeted for mutation. If a higher affinity is desired those amino acids that make the smallest contributions are selected; and vice versa, if a lower affinity is desired those amino acids that make the largest contributions are selected. If no amino acid discrimination can be made, or if mutations are not feasible, then the peptide length is the remaining variable.

10. Amino Acid Replacement, Addition or Deletion and Energy Minimization

The starting point for design is the lead peptide. As discussed above, the lead peptide is either defined computationally, or is defined by the high resolution structure of an existing peptide/protein complex. In both situations, the manipulations are similar.

The design of a peptide ligand having as a starting point a lead peptide involves three elementary operations: 1) the addition; 2) deletion; or 3) replacement of one type of amino acid by another (mutation). Other, more complex operations are accomplished by combining several elementary operations. Once the operation is made, the most probable conformation is selected by identifying the one with the lowest binding energy.

Amino Acid Addition

Amino acids can be added either at the amino or carboxy ends of the lead peptide. Additions at central positions are not considered explicitly because they can be accomplished by combining mutations with addition/deletions at either end. The procedure by which a new amino acid is added at the amino or carboxy terminus of the peptide can be viewed as a reptation movement in which the new amino acid samples different backbone and side chain orientations until it finds the one that minimizes the binding energy. Each orientation is dictated by a set of values for the backbone torsional angles $\phi$ and $\psi$, and the set of side chain dihedrals $\{\chi\}$.

Amino Acid Deletion

Amino acids can be deleted either from the amino or carboxy terminus of the lead peptide.

Amino Acid Mutation

Amino acid mutations can be performed at any position along the peptide sequence. They involve side chain replacement followed by energy minimization.

Energy Minimization

The search for the most probable conformation is equivalent to the search for the conformation that minimizes the Gibbs potential function $\Delta G_{ef}$. The probability of a single peptide conformation, defined by a specific set of side chain and backbone coordinates, is dictated by the Gibbs potential function, $\Delta G_{ef}$, specified by the enthalpy and entropy of solvation. $\Delta G_{ef}$ is a function of the side chain and backbone torsional angles. By definition, the conformational entropy of the peptide itself does not enter into the equation. $\Delta G_{ef}$ is the Gibbs energy function of a single conformation and should not be confused with the Gibbs energy of binding which includes all permissible conformations. The probability of any given conformation is given by the equation $$P_i = \frac{e^{-\Delta G_{ef,i}/R \cdot T}}{\sum_j e^{-\Delta G_{ef,j}/R \cdot T}}$$

where $e^{-\Delta G}_{ef,i}/RT$ is the Boltzman exponent for that conformation, and the sum in the denominator is the conformational partition function defined as the sum of the Boltzmann exponents of all conformations. The Gibbs potential function, $\Delta G_{ef}$, is used to identify the most probable conformation of a side chain or backbone. It should be noted that the energy minimization procedure used here involves enthalpic terms arising from intra- and intermolecular interactions as well as interactions with solvent, and the entropy of solvation.

Conformations are generated by systematically varying the dihedral angles between 0 and 360 degrees every 10 degrees. For backbone conformations the torsional angles are also varied every 10 degrees between 0 and 360 degress. Refinements are made by identifying conformations that are close to an energy minimum and reduce the rotation intervals. For simple situations an exhaustive search is possible. For most complicated situations standard search algorithms aimed at identifying the minima of functions used (e.g. gradient, simplex, steepest descent, etc.). Due to steric hinderances, not every conformation generated by rotation around a given bond is feasible. Thus, for each conformation, van der Waals conditions are checked by using the set of effective van der Waals radii MMII published by Iijima et al. (1987). Those conformations that exhibit van der Waals collisions are rejected. The Gibbs potential function $\Delta G_{ef}$ is calculated only for allowed conformations.

11. The Binding Gibbs Free Energy

Binding affinity is determined by the Gibbs free energy of binding, described in greater detail below. All energy computations presented here are based on a structural parameterization of the energetics described herein. The prior level of refinement of this parameterization is summarized in the following references: (Bardi et al., 1997; D'Aquino et al., 1996; Gomez et al., 1995(a); Gomez et al., 1995(b); Hilser et al., 1996(b); Luque et al., 1996). This structural parameterization provides the bulk of the Gibbs energy. However, for the level of accuracy required in this algorithm, additional terms are sometimes required. These additional terms include among others conformational restrictions due to charge density, an explicit parameterization of the conformational restrictions due to disulfide bridges or other covalent links, the dependence of the dielectric constant on solvent accessibility, the dependence of pK's of chemical groups on environment, parameterized standard values for the side chain accessibilities of all amino acids. Also, parametric descriptions of non-standard amino acids have been included.

The Gibbs energy of binding is composed of enthalpic and entropic components. Both components include contributions due to the formation of interactions between ligand and protein, and contributions due to changes in hydration. The enthalpic contributions are a function of the separation distance between atoms and the changes in atomic accessibility to the solvent. The entropy change contains solvent contributions which are also proportional to changes in solvent accessibility, and the reduction in conformational degrees of freedom. Electrostatic interactions and protonation/deprotonation events coupled to binding are also important and are included in the analysis. Changes in translational degrees of freedom are the same for different ligands and therefore do not contribute to discriminate between binding affinities even though they contribute to the actual affinity.

12. The Identification of the Conformation with the Lowest Energy

The identification of the conformation with the lowest energy utilizes an energy function similar to the parameterized Gibbs energy of binding, except that it does not contain the conformational entropy term. The reason is that in the energy minimization procedure, we are dealing with single conformations.

Each peptide conformation is defined by a set of side chain dihedrals $\{\chi\}$ and backbone torsional angles $\phi$ and $\psi$. The binding energy becomes a function of $\{\chi\}$, $\phi$ and $\psi$. Therefore, in the energy minimization routine the goal is to find the set of $\{\chi\}$, $\phi$ and $\psi$ for which the energy is a minimum. Several mathematical procedures are available for finding the minima of functions. The algorithm used in the methods of the invention does not rely on a particular minima location procedure.

13. The Identification of Peptide Binding Sites

If the binding site is not known, it is necessary to select some regions in the protein as being the most likely candidates to serve as peptide binding sites. This is done by mapping the protein surface in terms of the binding potential of each of its constituent atoms using the Woolford algorithm (described below).

Once the map of atomic binding potentials is obtained, it is transformed into a map of dipeptide binding potentials. This new map is obtained by selecting regions of dimensions similar to those found in dipeptides (typically ranging from 7.0 by 2.5 Å to 14 by 6.0 Å, which correspond to Gly—Gly and Trp—Trp). The geometrical dimensions and distribution of polar and nonpolar surface within each region is used to progressively determine the sequence of the most appropriate dipeptide. The general philosophy here is to increase the level of detail in the description of the candidate for lead dipeptide as the level of refinement advances. So, for example, a common protocol is to increase the level of detail according to the following order:

1) geometric dimensions of selected binding site;
2) fraction of polar and nonpolar surface;
3) topological distribution of polar and nonpolar surface;
4) full atomic description.

14. Structural Parameterization of Binding Energetics

In all cases presented here the Gibbs energy of binding, $\Delta G$, was calculated from the published crystallographic structures using procedures previously described (D'Aquino et al., 1996; Gomez et al., 1995(a); Gomez et al., 1995(b); Hilser et al., 1996(b); Luque et al., 1996). These calculations require the structures of the complex as well as the structures of the unligated protein and unligated inhibitor. In this approach, the generic portion of the Gibbs energy, $\Delta G_{gen}$, is calculated from a separate computation of its enthalpy and entropy components. This portion of the Gibbs energy contains those contributions typically associated with the formation of secondary and tertiary structure (van der Waals interactions, hydrogen bonding, hydration and conformational entropy). Additional contributions to the Gibbs energy of binding are not separated into enthalpic and entropic components. They include electrostatic and ionization effects, Gion, and the contribution of the change in translational degrees of freedom, $\Delta G_{tr}$, $$\Delta G = \Delta G_{gen} + \Delta G_{ion} + \Delta G_{tr}$$

Generic Contributions to Gibbs Energy

The most significant structural/solvation contributions to the total free energy of binding are contained in the term $\Delta G_{gen} = \Delta H_{gen} - T \cdot \Delta S_{gen}$ which is calculated by estimating separately its enthalpy and entropy components. The important structural changes for these calculations are the changes in apolar and polar solvent accessible surface areas ($\Delta ASA_{ap}$ and $\Delta ASA_{pol}$) and the distribution of interatomic distances between different atom types which determines the packing density.

The changes in accessible surface areas were calculated by implementing the Lee and Richards algorithm (Lee et al., 1971). In all calculations a solvent radius of 1.4 Å and a slice width of 0.25 Å were used.

In order to better define small differences in solvent accessibility between inhibitors or mutants, 64 different protein/inhibitor orientations with respect to the slicing plane are considered in the accessible surface area calculations. These orientations are generated by rotating the molecule around the x, y and z axis every 90 degrees. In this way, the resulting solvent accessibility for each atom is the numerical average of the values obtained for all molecular orientations. When the solvent accessibilities for unfolded conformations are needed, a set of free energy optimized values is used (Luque et al., 1996).

Enthalpic Component of the Generic Contribution to Gibbs Free Energy

In binding or folding, the bulk of the enthalpy change originates from the formation of internal interactions (van der Waals, hydrogen bonds, etc.) and the parallel desolvation of the interacting groups. Not surprisingly, the bulk of the enthalpy change scales both in terms of $\Delta ASA$ changes and the interatomic distances between the interacting groups. At the reference temperature of 60° C. it can be written as (Hilser et al., 1996(b)):

$$\Delta H_{gen}(60) = (\alpha_{ap} \cdot \beta_{ap} + U_{ap}^6) \cdot \Delta ASA_{ap} + (\alpha_{pol} + \beta_{pol} \cdot U_{pol}^6) \cdot \Delta ASA_{pol} + \beta_{mix} \cdot U_{mix}^6 \cdot \Delta ASA_{Total}$$

where the empirical coefficients $\alpha$ and $\beta$ have been estimated from an analysis of the protein thermodynamic database and are equal to $\alpha_{ap} = -12.96$, $\beta_{ap} = 25.34$, $\alpha_{pol} = 24.38$, $\beta_{pol} = 16.57$ and $\alpha_{mix} = 16.42$. The terms $U_i$ represent the packing density of apolar, polar and mixed atoms and is equal to the energy weighted average of the ratio between the separation distance at the minimum in the potential well and the actual separation between atom types. The above equation can be generalized to arbitrary atom types as:

$$\Delta H_{gen}(60) = \Sigma (\alpha_i + \beta_i \cdot U_i^6) \cdot \Delta ASA_i$$

For the average packing density in proteins, $\Delta H_{gen}(60)$ is well approximated by:

$$\Delta H_{gen}(60) = -8.44 \cdot \Delta ASA_{ap} + 31.4 \cdot \Delta ASA_{pol}$$

At any other temperature, $\Delta H_{gen}(T)$ is obtained from the standard thermodynamic equation:

$$\Delta H_{gen}(T) = \Delta H_{gen}(60) + \Delta C_p \cdot (T - 333.15)$$

$\Delta H_{gen}$ needs not be equal to the experimental enthalpy. For example, it has been shown that for binding processes in which protons are either released or absorbed the measured enthalpy depends on the ionization enthalpy of the buffer (Gomez et al., 1995(b)).

Entropic Component of the Generic Contribution to Gibbs Free Energy

In the calculation of the entropy change two primary contributions are included, one due to changes in solvation and the other due to changes in conformational degrees of freedom ($\Delta S_{gen}(T) = \Delta S_{solv}(T) + \Delta S_{conf}$). The entropy of solvation is temperature dependent while the conformational entropy is essentially a constant at different temperatures. The entropy of solvation can be written in terms of the heat capacity if the temperatures at which the apolar and polar hydration entropies are zero ($T^*_{S,ap}$ and $T^*_{S,pol}$) are used as reference temperatures:

$$\Delta S_{solv}(T) = \Delta S_{solv,ap}(T) + \Delta S_{solv,pol}(T)$$

$$\Delta S_{solv}(T) = \Delta C_{p,ap} \cdot \ln(T/T^*_{S,ap}) + \Delta C_{p,pol} \cdot \ln(T/T^*_{S,pol})$$

$T^*_{S,ap}$ has been known to be equal to 385.15K for some time (Baldwin, 1986; Murphy et al., 1992(b)) and $T^*_{S,pol}$ has been recently found to be close to 335.15K (D'Aquino et al., 1996). While the entropy of apolar solvation appears to be additive, the situation for polar solvation is known to depend on the number and proximity of polar functional groups in the molecule (Cabani et al., 1981).

Conformational entropies upon binding or folding are evaluated by explicitly considering the following three contributions for each amino acid:

1) $\Delta S_{bu \to ex}$, the entropy change associated with the transfer of a side chain that is buried in the interior of the protein to its surface;
2) $\Delta S_{ex \to u}$, the entropy change gained by a surface exposed side chain when the peptide backbone changes from a unique conformation to an unfolded conformation; and,
3) $\Delta S_{bb}$, the entropy change gained by the backbone itself upon unfolding from a unique conformation.

The magnitude of these terms for each amino acid has been estimated by computational analysis of the probability of different conformers as a function of the dihedral and torsional angles (D'Aquino et al., 1996; Lee et al., 1994; Luque et al., 1996).

Since some ligands considered are not peptides, a special parameterization can be implemented to account for the change in conformational degrees of freedom between the bound and free forms of the ligand molecules. As shown in FIG. 10, the total number of atoms as well as the number of rotatable bonds varies between ligands. In general, the conformational entropy of the ligand free in solution will be proportional to the number of rotatable bonds. However, for a given number of rotatable bonds, excluded volume effects will increase with the total number of atoms in the molecule. Therefore, as a first approximation, the conformational entropy change of non-peptide ligands upon binding, $\Delta S_{np}$, was considered to be a linear function of the number of rotatable bonds ($N_{rb}$) and total number of atoms ($N_{atoms}$):

$$\Delta S_{np} = k_1 \cdot N_{rb} + k_2 \cdot N_{atoms}$$

The coefficients $k_1$ and $k_2$ were estimated from an experimental database of non-peptide ligands. The coefficient $k_1$ was found to be equal to $-1.76$ cal/K•mol which is close to the conformational entropy value observed for C—C bonds in long chain paraffins (Schellman, 1955(a); Schellman, 1955(b)). The coefficient $k_2$ was found to be equal to 0.414 cal/K•mol and essentially accounts for the conformational entropy restrictions in the free ligand due to excluded volume.

The heat capacity change is a weak function of temperature and has been parameterized in terms of changes in solvent accessible surface areas ($\Delta\Delta ASA$) since it originates mainly from changes in hydration (Gomez et al., 1995(a); Gomez et al., 1995(b); Murphy et al., 1992(a)):

$$\Delta C_p = \Delta C_{p,ap} + \Delta C_{p,pol}$$

$$\Delta C_p = a_C(T) \cdot \Delta\Delta ASA_{ap} + b_C(T) \cdot \Delta\Delta ASA_{pol} + c_C(T) \cdot$$

where the coefficients $a_C(T) = 0.45 + 2.63 \times 10^{-4} \cdot (T-25) - 4.2 \times 10^{-5} \cdot (T-25)^2$ and $b_C(T) = -0.26 + 2.85 \times 10^{-4} \cdot (T-25) + 4.31 \times 10^{-5} \cdot (T-25)^2$. The hydration of the hydro group in aliphatic hydroxyl side chains (Ser and Thr) appears to contribute positively and not negatively to $\Delta C_p$ as previously assumed (0.17 cal•K$^{-1}$•mol$^{-1}$ Å 2 at 25° C.) (Gomez et al., 1995(b)). In the equation above, $\Delta\Delta ASA$ changes are in Å 2 and the heat capacity in cal•K$^{31}$ $^1$•mol$^{-1}$. In general, for low temperature calculations (T<80° C.) the temperature independent coefficients are sufficient (Gomez et al., 1995(a); Gomez et al., 1995(b)). Specific effects like heat capacity changes associated to changes in protonation, differential binding of ligands or denaturants, etc., need to be considered individually (Gomez et al., 1995(a); Gomez et al., 1995(b)).

Ionic and Electrostatic Contributions to Gibbs Free Energy

Two types of electrostatic effects need to be considered in this situation. Coulombic contributions due to the interactions between charged sites, and the self energy arising from charging a single site or alternatively the self energy arising from transferring a charge between environments with different dielectric constants. These electrostatic contributions were computed as described by García-Moreno (García-Moreno, 1995) using the standard equation:

$$\Delta G_{el} = \sum_i \frac{332 \cdot Z_i^2}{2 \cdot r_i} \left( \frac{1}{A} - \frac{1}{A_{ref}} \right) + 332 \cdot Z_i \sum_j \frac{Z_j}{A \cdot r_{ij}}$$

where Z is the charge, $r_i$ the radius of the charged particle, $r_{ij}$ the separation between two charges, A and $A_{ref}$ the attenuation parameters in the complex and reference. These parameters incorporate dielectric and screening effects as discussed in (García-Moreno, 1995) and (García-Moreno et al., 1997).

Protonation effects are treated as described before (Gomez et al., 1995(b)) from a knowledge of the pKa of the groups that change ionization state upon binding.

Translational Entropy Contribution to Gibbs Energy

The association of two or more molecules reduces the translational degrees of freedom available to those molecules. There has been considerable discussion regarding the exact magnitude of this term since no precise calculations are available (see for example Janin, 1995; Kauzmann, 1959; Murphy et al., 1994). In our work (Gomez et al., 1995(b); Murphy et al., 1994), we have found that the value that best account for experimental results is the cratic entropy proposed by Kauzmann (Kauzmann, 1959). For the formation of a bimolecular complex the cratic entropy is equal to $-8$ cal/K•mol which amounts to approx. 2.4 kcal/mol at 25° C.

Calculation of Residue Stability Constants

An important set of parameters for mapping the structural stability of different regions of a protein is given by the apparent residue stability constants. For any given residue, the apparent stability constant per residue, $K_{f,j}$, is defined as the ratio of the probabilities of all states in which that residue is folded, $P_{f,j}$, to the probabilities of the states in which that same residue is not folded:

$$K_j = \frac{\sum_{\substack{\text{(states with} \\ \text{residue } j \\ \text{folded)}}} P_i}{\sum_{\substack{\text{(states with} \\ \text{residue } j \\ \text{not folded)}}} P_i} = \frac{P_{f,j}}{P_{nf,j}}$$

The apparent stability constant per residue, $K_{f,j}$, is the quantity that one will measure if it were possible to experimentally determine the stability of the protein by monitoring each individual residue. Therefore, variations in stability constants per residue permit an evaluation of structural stability differences between regions of the protein. In many cases, hydrogen exchange protection factors measured by NMR permit an experimental determination of the apparent stability constants per residue (Hilser et al., 1996(a); Hilser et al., 1997(a); Hilser et al., 1997(b)).

EXAMPLE 1

Prediction of Binding Affinities of HIV-1 Protease Inhibitors

HIV-1 protease has been the subject of intense research during the last few years. The development of protease inhibitors is a major endeavor for several pharmaceutical companies, since the successful inhibition of this protein arrests viral maturation. Inhibitors of the HIV-1 protease are substrate analogues, i.e., they function by competing with the natural substrates for the active site. Because substrates are rapidly hydrolyzed by the protease, crystallographic structures of enzyme/substrate complexes cannot be obtained, thus creating additional obstacles to the design process.

Figure 9:
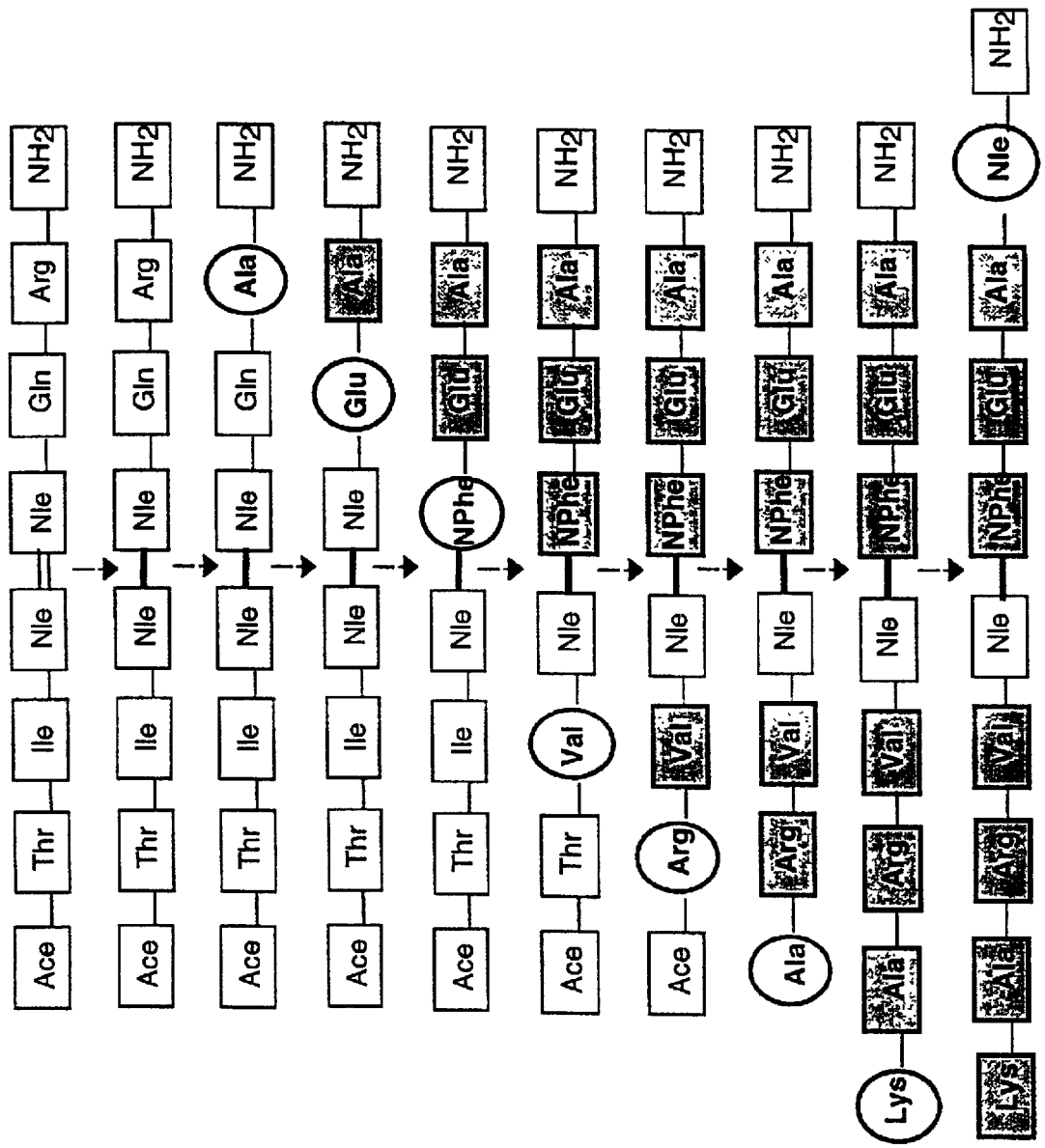
FIG. 9 is an illustration of the design of HIV-1 protease substrate using and inhibitor as the lead compound.
Figure 10A:
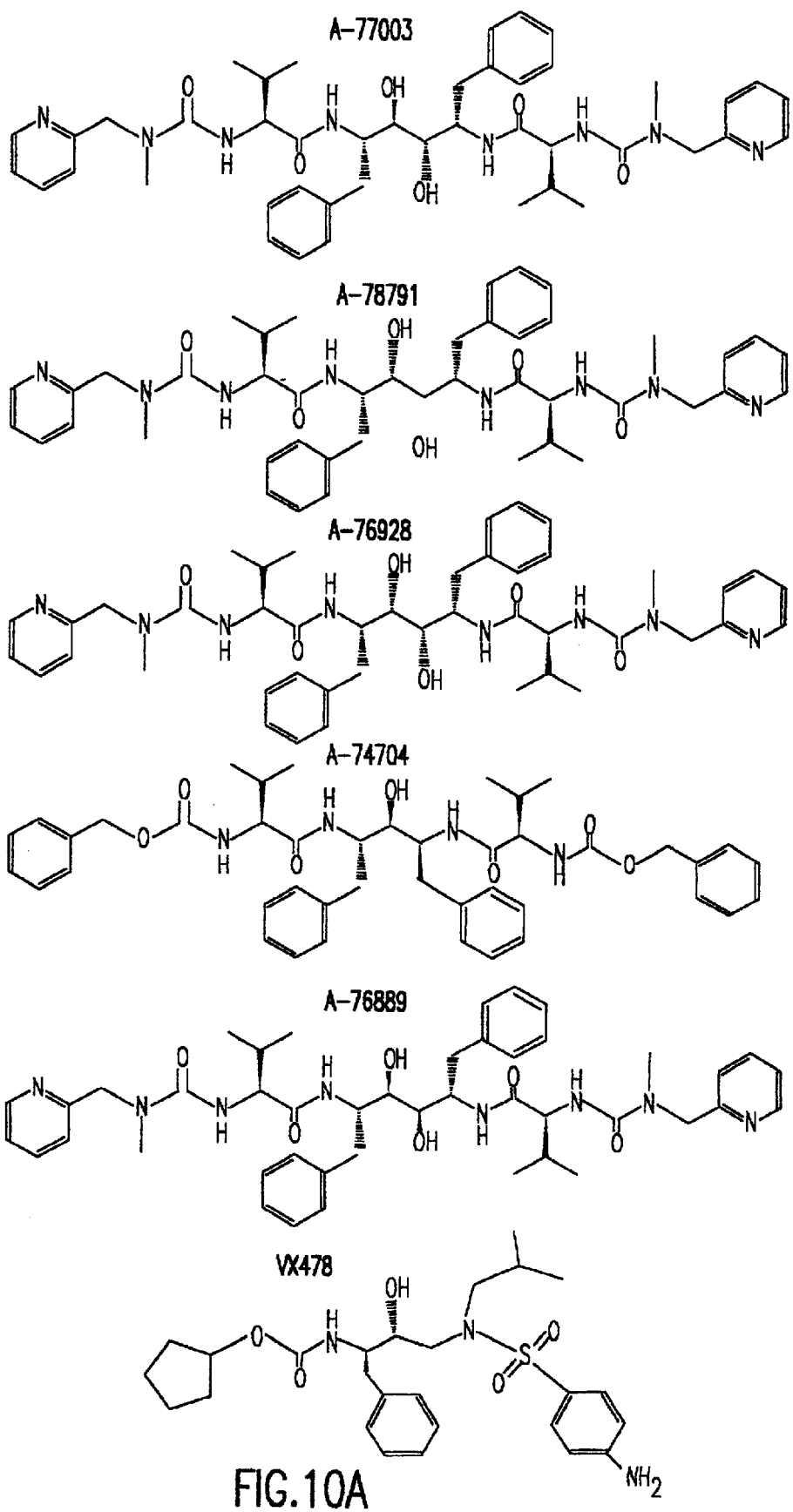
FIG. 10 is a series of chemical structures of the thirteen HIV-1 protease inhibitors considered in this paper. The original references for each inhibitor are given in the text.
Figure 10B:
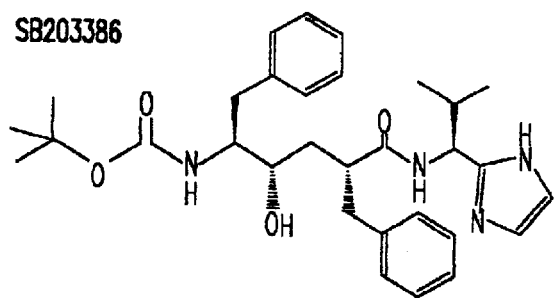
Figure 10B:
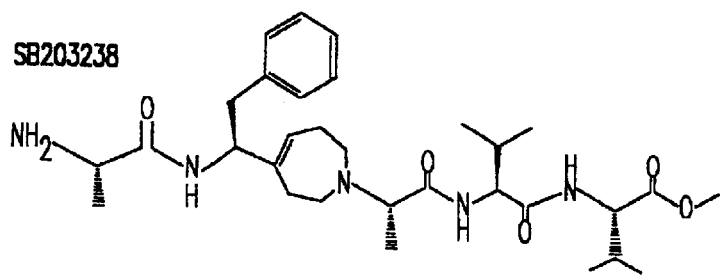
Figure 10B:
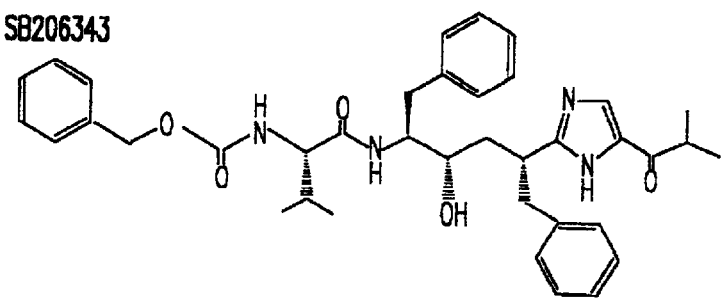
Figure 10B:
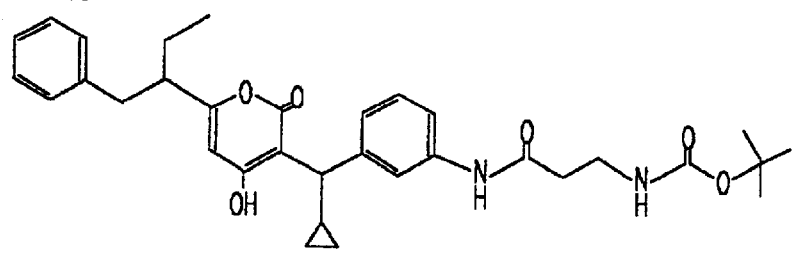
Figure 10B:
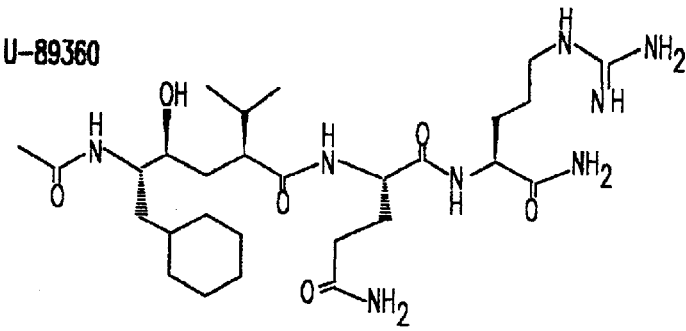
Figure 10C:
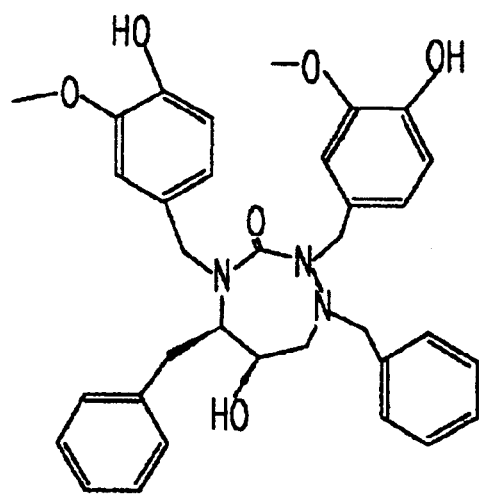
Figure 10C:
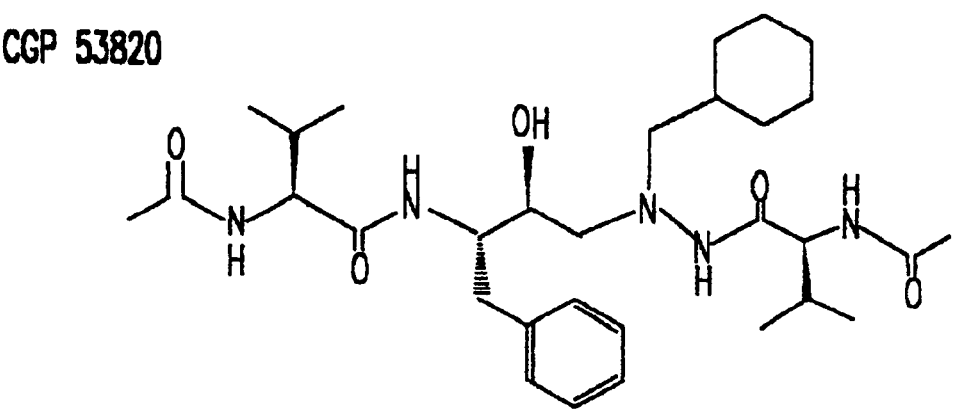

In the example presented here, the known structure of the HIV-1 protease with the inhibitor Ace-Thr-Ile-Nle-Nle-Gln-Arg-NH$_2$ (pdb file 4hvp) is used to generate the structure of the widely used chromogenic substrate Lys-Ala-Arg-Val-Nle-NPhe-Glu-Ala-Nle-NH$_2$. In the chemical formulas, Nle stands for norleucine, and NPhe for p-nitro-phenylalanine. The inhibitor has six amino acids with a reduced peptide bond between Nle 3 and Nle 4. The substrate, on the other hand, has nine amino acids, only one of which (Nle 3) is conserved from the inhibitor. Accordingly, the design of the substrate is made by using the inhibitor as a lead peptide and by implementing a combination of mutations and peptide extensions at both the carboxy and amino terminus (FIG. 9).

Figure 8:
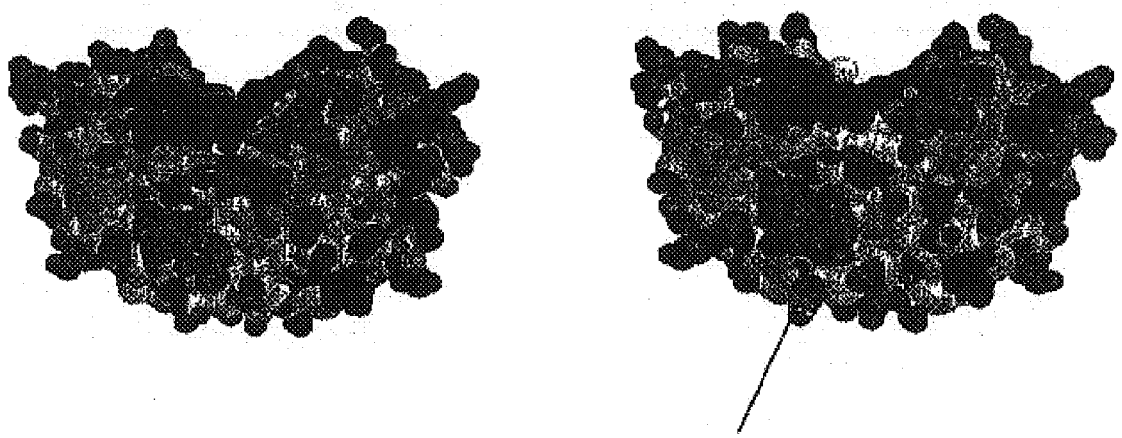
FIG. 8 is an illustration of the binding surface of HIV-1 protease calculated using the Woolford algorithm.

The Woolford algorithm was applied to the crystallographic structure of HIV-1 and requested to search for binding targets without a priori specifying the location of the natural binding site. Woolford correctly predicts the location of the main binding site including the participation of amino acids from both the flap region and the main body of the protein (FIG. 8). It should be noted that the algorithm also predicts the presence of additional sites with target potential. These additional sites represents secondary potential targets which may be explored for new drug development.

The following study of the binding of HIV-1 protease to known inhibitors of HIV-1 protease illustrates energy parameterization functions which can be used in the method of the invention. However, the invention is not limited to the use of these functions. Those skilled in the art can use other functions.

Several HIV-1 protease inhibitors are already in clinical use and have shown significant promise in combination therapies that include nucleoside inhibitors or several protease inhibitors. A significant clinical outcome has been the emergence of viral strains that exhibit resistance to multiple HIV-1 protease inhibitors (Condra et al., 1995, Ho et al., 1994, Kaplan et al., 1994, Roberts, 1995, Tisdale, 1996). Loss of sensitivity to protease inhibitors occurs because the resistant viral strains encode for protease molecules containing specific amino acid mutations that lower the affinity for the inhibitors, yet maintain sufficient affinity for the substrate. The origins of the resistance are still unclear. While some of the observed mutations are located directly in the binding site, other mutations are far away from the binding pocket. It is also apparent that different inhibitors elicit different mutational patterns and that the patterns of cross resistance are not the same, despite the fact that all inhibitors target the same binding site.

It would be useful to predict the binding affinity of a given molecule to HIV protease. The method described herein can be used to make such predictions.

Structural parameterization of the binding and folding energetics described below accounts quantitatively for the binding of thirteen HIV-1 protease inhibitors for which high resolution structures are available (A77003, A78791, A76928, A74704, A76889, VX478, SB203386, SB203238, SB206343, U100313, U89360, A98881, CGP53820). The binding free energies for the inhibitors are predicted with a standard deviation of ±1.1 kcal/mol or ±10%. Furthermore, the formalism correctly predicts the observed change in inhibition constant for the complex of A77003 and the resistant protease mutant V82A, for which the high resolution structure is also available. The analysis presented here provides a structural mapping of the different contributions to the binding energetics. Comparison of the binding map with the residue stability map indicates that the binding pocket in the protease molecule has a dual character, one half of the binding site is defined by the most stable region of the protein, while the other half is unstructured prior to inhibitor or substrate binding. This characteristic of the binding site accentuates cooperative effects that permit mutations in distal residues to have a significant effect on binding affinity. These results permit an initial assessment of the effects of mutations on the activity of protease inhibitors.

The development of successful strategies for structure-based molecular design requires the ability to accurately predict binding affinities from structural considerations. Structural parameterization of the folding and binding energetics of proteins and peptides is known (DAquino et al., 1996; Gomez et al., 1995(a); Gomez et al., 1995(b); Hilser et al., 1996(b); Luque et al., 1996). This parameterization has been shown to be accurate enough to predict the helical propensities of amino acids with an accuracy better than 0.2 kcal/mol (Luque et al., 1996), and to correctly predict the global stability of proteins and the stability constants per residue as reflected in the pattern of NMR-detected hydrogen exchange protection factors (Hilser et al., 1996(a); Hilser et al., 1997(a); Hilser et al., 1997(b)).

This methodology has been applied to the association of thirteen different inhibitors of the HIV-1 protease for which high resolution crystallographic structures are available. Inhibition constants for these inhibitors, some of which are in clinical trials or clinical use, are available. The thirteen inhibitors are: A77003, A78791, A76928, A74704, A76889, VX478, SB203386, SB203238, SB206343, U100313, U89360, A98881, CGP53820 (Abdel-Meguid et al., 1994; Erickson et al., 1990; Fassler et al., 1993; Hoog et al., 1995; Kim et al., 1995; Lin et al., 1993; Madhusoodan et al., 1994; Thaisrivongs et al., 1995; Thompson et al., 1994). Their structures are shown in FIG. 10. The analysis was also performed on the complex of A77003 with the inhibitor resistant protease mutant V82A for which the high resolution is available (Baldwin et al., 1995).

The development of a new generation of protease inhibitors that effectively addresses the issue of resistance requires a better understanding of the interactions, both between protease and inhibitors and between protease and substrates. The sequencing of viral isolates from patients undergoing therapy with protease inhibitors has allowed identification of the location and character of the mutations but has provided no molecular description of the origin of resistance. The analysis presented here provides a detailed structural mapping of the binding energetics for thirteen different protease inhibitors and a quantitative account of the effects of V82A mutation on the affinity for the inhibitor A77003. As such, these studies should help in the development of a new generation of inhibitors.

The set of residue stability constants for the HIV-1 protease molecule was calculated from structure according to the COREX algorithm (Hilser et al., 1996(a), Hilser et al., 1997(a), Hilser et al., 1997(b)). A total of 126,496 states with degrees of folding ranging from the native to the completely unfolded states were used in these calculations. The states were generated by using a sliding block of windows of 16 amino acids each. The Gibbs energy, partition function and relative probability of the 126,496 states were calculated using the structural parameterization of the energetics described above.

Figure 11:
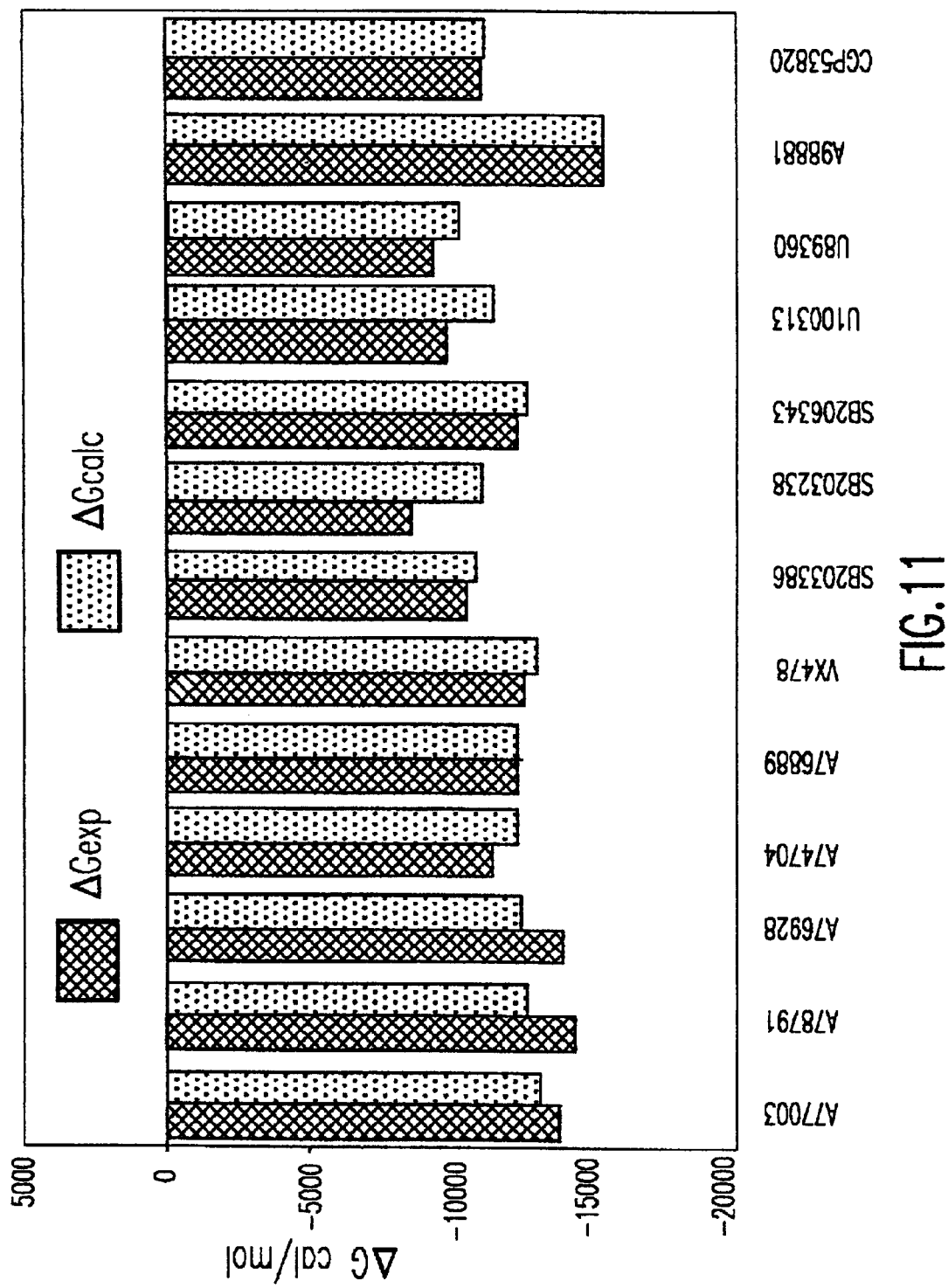
FIG. 11 shows predicted and experimental binding affinities for the thirteen HIV-1 protease inhibitors considered here. The calculations were performed as described using the corresponding PDB files for each complex (A77003: 1hvi, A78791: 1hvj, A76928: 1hvk, A74704: 9hvp, A76889: 1hvl, VX478: 1hpv, SB203386: 1sbg, SB203238: 1hbv, SB206343: 1hps, U100313: 2UPJ, U89360: 1gno, A98881: 1pro, CGP53820: 1hih).

FIG. 11 shows the predicted and experimental binding affinities for the thirteen HIV-1 protease inhibitors considered here. For those protease/inhibitor complexes for which the structure of the free enzyme is available the calculations were performed by using both, the structure of the free enzyme (Spinelli et al., 1991), as well as the structure of the enzyme in the complex but without the inhibitor, as the unligated protein. The results were equivalent in both cases, the differences in Gibbs energies being smaller than 0.5 kcal/mole on the average. For those cases in which deviations were larger (pdb files 2upj, 1hvi, 1hvj, 1hvk, 9hvp) the deviations were traced to the side chain conformations of Phe 53B, Lys 55B, Arg 41A and Arg 41B. These side chains are solvent exposed and far away from the binding site, indicating that the conformational differences are not related to the inhibitor. The statistical analysis of the data reveals that the free energies of binding are predicted with a standard deviation of ±1.1 kcal/mol and a standard error of 0.3 kcal/mol. The standard deviation amounts to a relative uncertainty of ±10%. The correlation analysis between the experimental and predicted ΔG values yields a slope of 0.982 with a correlation coefficient of 0.85. The structural predictions show no systematic deviations and are accurate enough to permit an examination of the different contributions to the binding energetics.

According to the analysis, the binding of the thirteen inhibitors to the enzyme is dominated by the hydrophobic effect. Upon binding, not only the inhibitor itself but protease residues located in the binding pocket, bury a significant non-polar surface from the solvent. In fact, the average fraction of non-polar area buried from the solvent upon binding is 0.737±0.02, which is much higher than the fraction buried by a typical globular protein upon folding (between 0.55–0.60). Not surprisingly, the major contribution to the Gibbs energy of binding is given by the favorable entropy resulting from the release of water molecules associated with the desolvation of those surfaces. On the other hand, the enthalpic contributions due to those generic effects are unfavorable at room temperature since they are dominated by the positive enthalpy of desolvating hydrophobic groups. The breakdown of the energetics is summarized in Table 1.

The heat capacity values listed in Table 1 are of the same magnitude as those measured for other protease inhibitors (Gomez et al., 1995). The magnitude of the heat capacity changes is dominated by changes in solvation of polar and non-polar groups and is not expected to be significantly affected by other interactions (Gomez et al., 1995). The enthalpy values listed in Table 1 include only generic contributions and cannot be compared directly to experimental values since electrostatic and other contributions are not included. This generic enthalpy is composed primarily of two opposite effects, a favorable component due to the formation of van der Waals, hydrogen bonds and other interactions between inhibitor and protease, and an unfavorable component due to desolvation. Due to the highly hydrophobic character of the inhibitors the dominant term is the desolvation term. This is, however, not a general phenomenon as demonstrated for the binding of some peptide inhibitors which exhibits a favorable enthalpy under certain conditions (Gomez et al., 1995(b)). As shown in Table 1, the structure/solvation terms included in $\Delta G_{gen}$ make the largest contribution to the total Gibbs energy of binding. All the inhibitors are highly hydrophobic and lack polar groups. For this reason, electrostatic interactions are predicted to contribute very little to the binding Gibbs energy. The only significant electrostatic contribution described by equation 10 arises from the change in the environmnet of Asp 25, Asp 29 and Asp 30 which may contribute up to 0.7 kcal/mol depending on the inhibitor. This contribution arises from the transferring of the charge from water to an environment with a somewhat lower dielectric constant. According to the experimental results of García-Moreno et al (García-Moreno et al., 1997) the dielectric constant in the interior of a protein is no lower than ~15. According to these authors, the dielectric constant of different protein regions ranges between 15 and 78.5 depending on the solvent accessibility.

Structural Mapping of Protease Residues Contributing to Binding Affinity

Figure 12A:
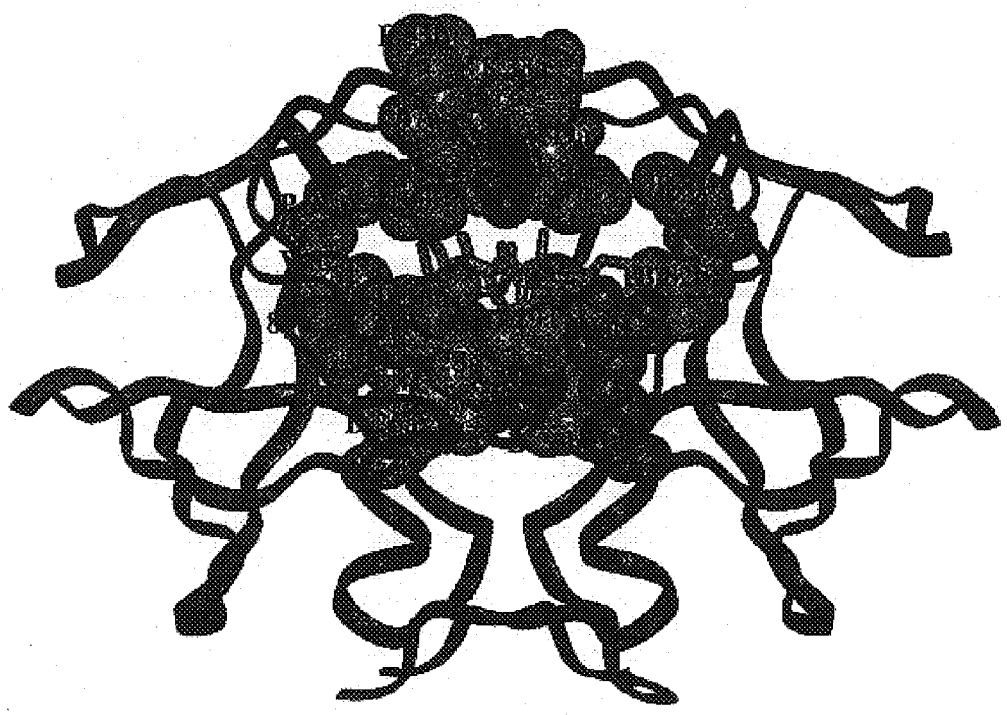
FIGS. 12A and 12B are two different views of the amino acid residues in the binding pocket of the HIV-1 protease molecule that contribute more than 0.1 kcal mol to the Gibbs energy of binding. The residues depicted in red contribute between −0.7 and −0.9 kcal/mo; the residues depicted in orange between −0.5 and −0.7 kcal/mol; the residues depicted in yellow between −0.3 and −0.5 kcal/mol; and the residues depicted in green −0.1 and −0.3 kcal/mol. As a guide to the eye, the inhibitor A77003 is shown using a sticks representation.
Figure 12B:
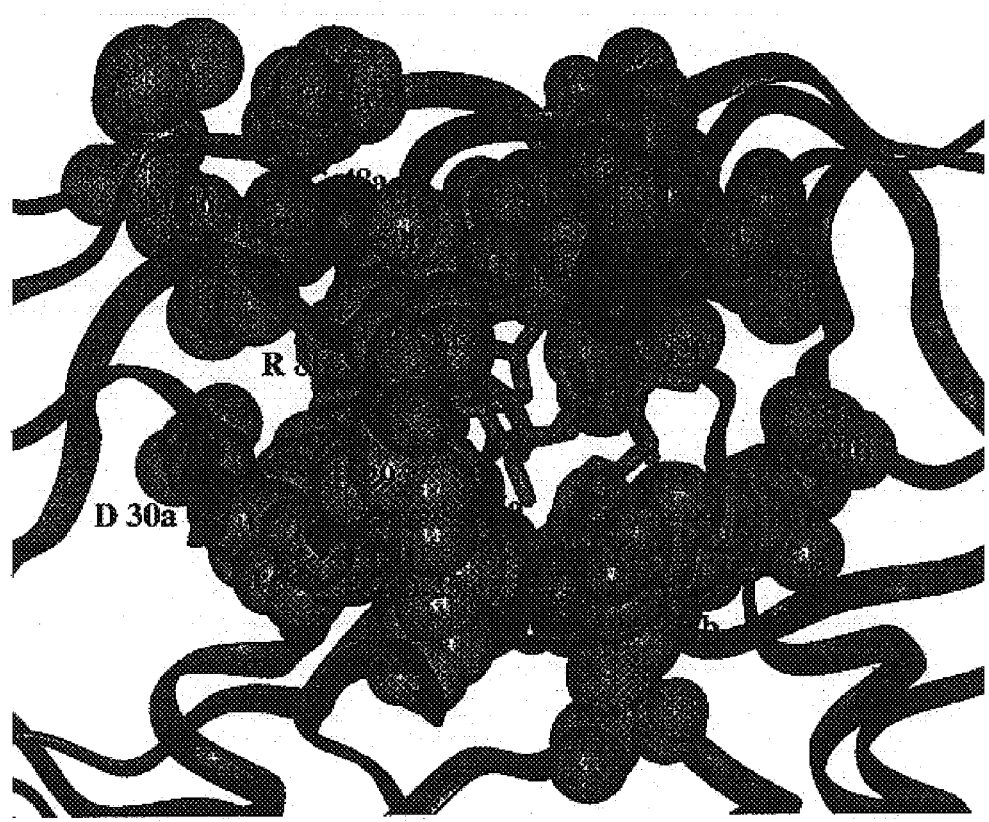

For the entire set of inhibitors, essentially the same set of protease residues, albeit with different strength, were observed to contribute to the binding energetics, reflecting the fact that they have been targeted to the same site on the molecule. Table 2 summarizes those amino acids in the protease molecule that contribute more than 0.1 kcal/mol to the total free energy of binding for at least one of the inhibitors. The values listed in the Table do not include the contribution corresponding to the inhibitor (~55% of the total Gibbs energy of binding) or the translational entropy that cannot be ascribed to a particular amino acid. FIGS. 12A and 12B shows the location of those amino acids in the protease structure.

From an energetic standpoint, the binding pocket is defined by amino acids belonging to four non-contiguous regions in sequence. Amino acids in the region containing the catalytic Asp group (Asp25, Gly27, Ala28, Asp29, Asp30), the so-called flap region (Met 46, Ile 47, Gly 48, Gly 49, Ile 50), the strand between residues 80–86 (Pro 81, Val 82, Ile 84) and Arg8 which contributes significantly to the binding energetics. Due to the chemical structure of the inhibitors, both chains in the protease molecule contribute in a more or less symmetrical fashion to the total Gibbs energy of binding. In all cases the region containing the catalytic Asp group is the major contributor to the binding energetics.

Structural Stability of Protease Residues Contributing to Inhibitor Binding

Figure 13:
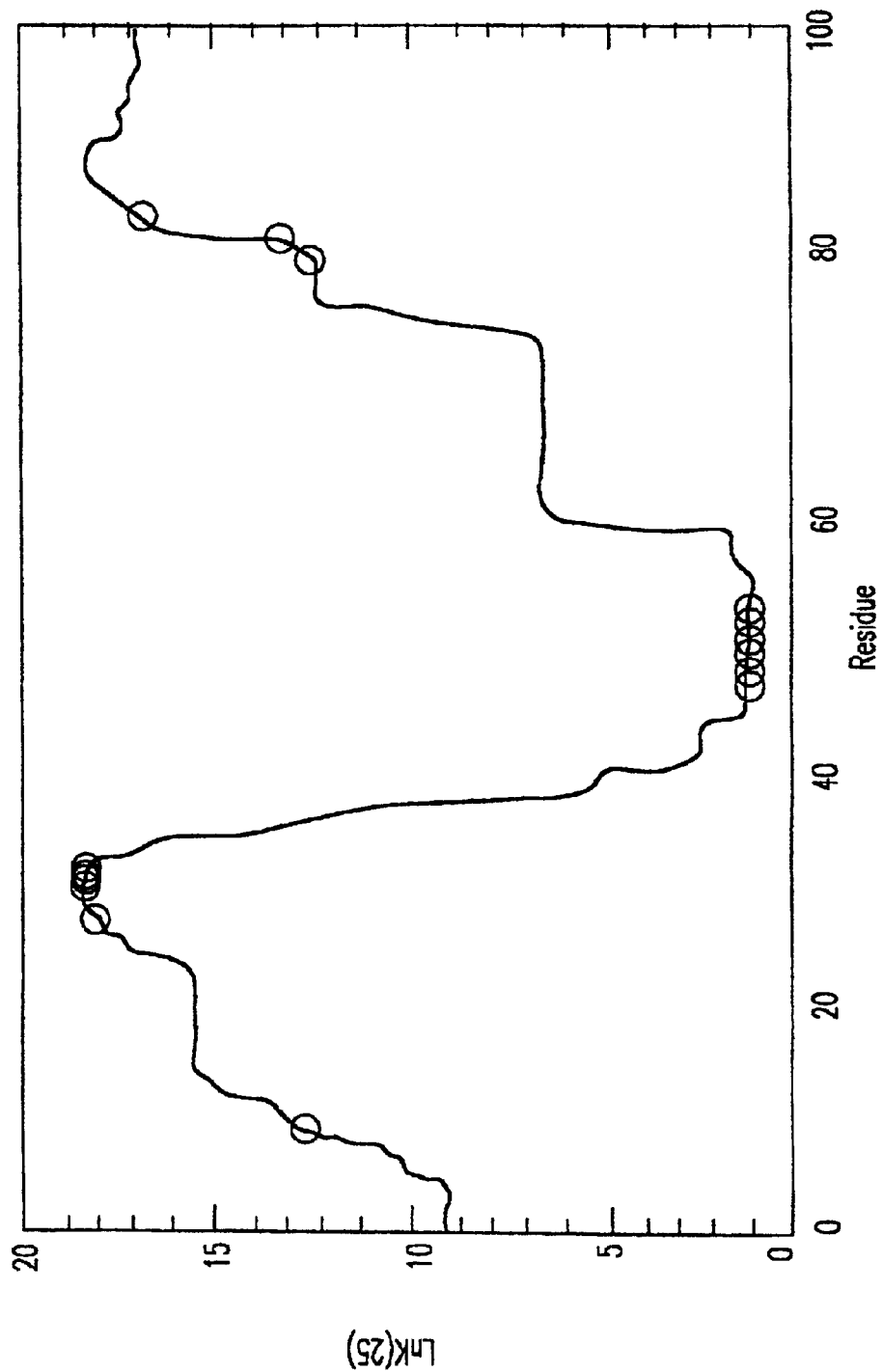
FIG. 13 show calculated residue stability constants for the HIV-1 protease molecule. These constants were calculated according to the COREX algorithm (Hilser et al., 1996(a); Hilser et al., 1997(a); Hilser et al., 1997(b) and map the protein molecule in terms of the structural stability of different regions. The circles indicate the location of the residues that contribute more than 0.1 kcal/mol to the Gibbs energy of inhibitor binding (Table 2).

FIG. 13 displays the calculated residue stability constants for the HIV-1 protease molecule. These constants map the protein molecule in terms of the structural stability of different regions (Hilser et al., 1996(a); Hilser et al., 1997(a); Hilser et al., 1997(b)). Protein residues with a high probability of being in the native conformation are characterized by high stability constants while residues that are most likely to be unstructured have low stability constants.

Two regions of the HIV-1 protease molecule are predicted to have the highest stability. The region including residues 13–32 and the region including residues 82–92. These two regions are distant in sequence but close in three dimensional space and define, to a significant extent, the hydrophobic core of the molecule. Portions of these two regions (residues 23–29 in the amino terminus and 86–99 in the carboxy terminus) as well as the first nine residues in the sequence are predicted to contribute significantly to the dimerization interface. This region of the protein is predicted to be folded and well structured in the vast majority of conformational states that are accessible to the protease under native conditions. The active site triad (Asp 25, Thr 26, Gly 27) is located in the most stable part of the molecule as shown in FIGS. 12A and 12B. This conclusion agrees with the results of the crystallographic analysis which identify this area of the molecule as quite rigid due to a dense network of hydrogen bonds (Wlodawer et al., 1993). Residues 82–92 comprise most of the well defined and highly stable h' helix. Conversely, the region between residues 40–60, which corresponds to the flap, is characterized by very low stability constants per residue and is predicted to be unstructured even under native conditions. In the complexes, the flap is stabilized by its interactions with the inhibitors. Similar results were obtained with the structure of the free protein (pdb file 1hhp) or with protein structures obtained from complexes by removing the inhibitor coordinates. This observation suggests that in the protease/inhibitor complex the flap is stabilized by interactions with the inhibitor and not with the protein.

FIGS. 12A, 12B, and 13 also indicate the location of the residues that contribute significantly to the Gibbs energy of binding. It is clear that the binding site is made up of residues belonging to both the most and the least stable regions of the protease molecule. This dual character of the binding pocket defines one of the most fundamental features of inhibitor binding to the protease molecule. Essentially, half of the binding site is preformed while the other half is formed during binding. The most stable region (containing binding site components Asp 25, Gly 27, Ala 28, Asp 29, Asp 30, Pro 81, Val 82, Ile 84) is essentially locked in a binding-competent conformation before binding occurs. The flap region, on the other hand, (containing binding site components Met 46, Ile 47, Gly 48, Gly 49, Ile 50) is largely unstructured before binding and is forced into a unique conformation by its interaction with the inhibitor. For this reason, protease residues not in direct contact with the inhibitor but capable of affecting, structurally or energetically, the facility with which the flap adopts its bound conformation will influence the overall binding energetics.

The Molecular Basis of Protease Resistance

The binding energetics described above provide some insights into the nature of the changes in HIV-1 protease mutants that have been observed to elicit in vivo resistance to multiple inhibitors. Several mutations have been identified in viral isolates from patients treated with protease inhibitors. For example, treatment with Ro31-8959 (saquinavir) has been shown to consistently induce the double mutant G48V +L90M (Roberts, 1995). In vitro selection of mutants by A77003 include V82I, M46L, M46F, V32I, V32I+V82I and R8Q (Kaplan et al., 1994). Resistant variants to VX478 that have been identified are M46I and I50V (Schinazi et al., 1996; Tisdale, 1996). A recent study has shown that four mutations (M46I+L63P+V82T+I84V) are sufficient to elicit cross resistance to the inhibitors MK639, XM323, A80987, Ro31-8959, VX478 and SC52151 (Condra et al., 1995). Some of these mutations are located on the binding pocket and are thought to affect the binding affinity by a direct alteration of protease/inhibitor interactions. Other mutations are at distant locations and are expected to affect affinity by cooperative interactions.

In general, mutations in HIV-1 protease may affect the binding energetics by a direct interaction with the inhibitor, by a cooperative effect in which the mutated amino acid does not interact directly with the inhibitor but affects interactions between protease residues that elicit an altered protease/ inhibitor interaction, or by some combination of both. For example, some mutations are located either in the flap or the hinge region and some of them are distal from the binding site (e.g. L63P, A71V). As discussed above, the flap is essentially disordered in the free enzyme. Therefore, if a mutation induces a substantial energy barrier for the flap to adopt its bound conformation, it will affect the binding affinity even if the mutation is distal from the binding pocket. Mutations like L63P or A71V will decrease the conformational degrees of freedom of that region and make some conformations unaccessible or energetically unfavorable (DAquino et al., 1996).

Figure 14:
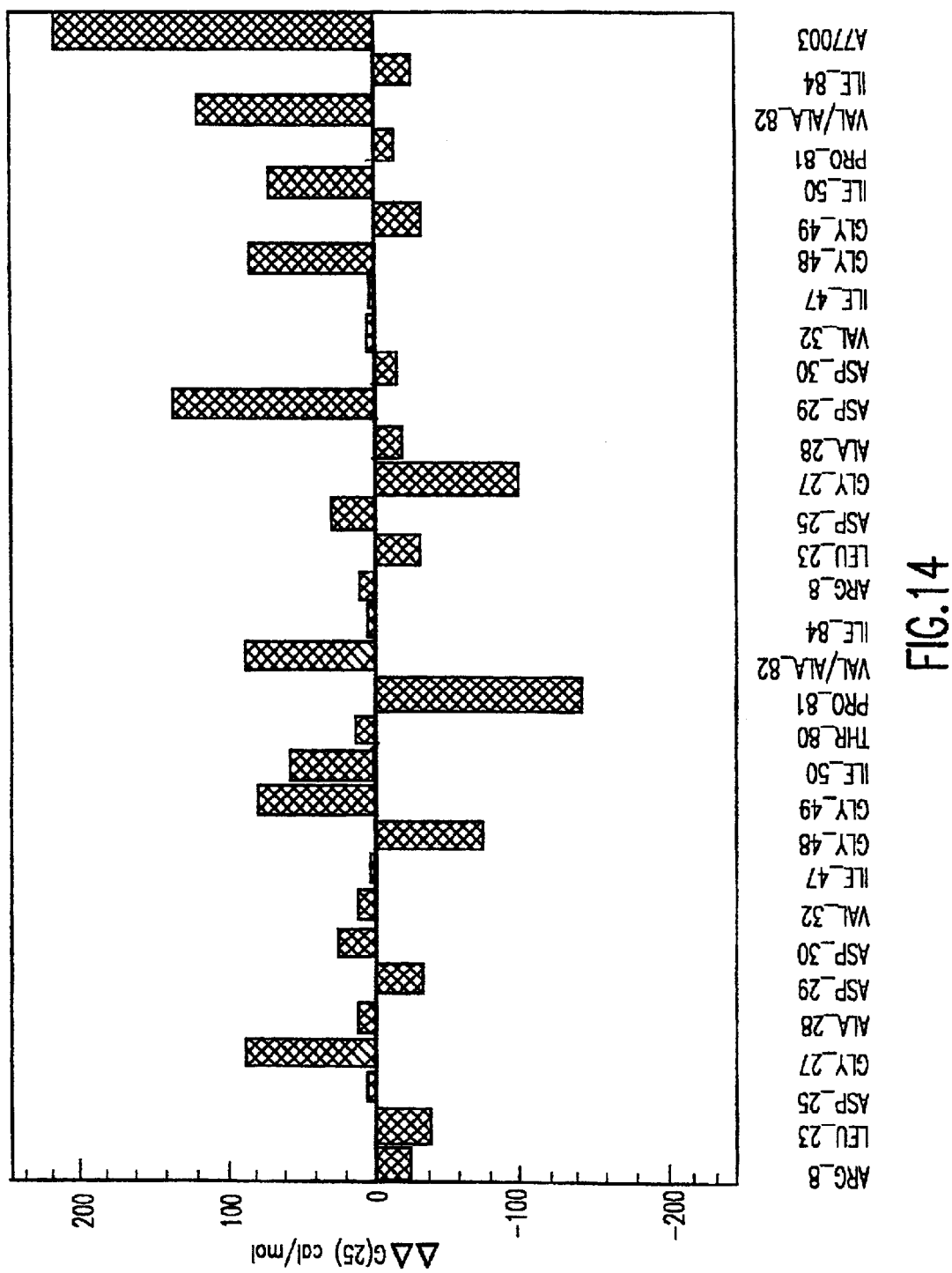
FIG. 14 show the difference in the HIV-1 protease residue contribution to the Gibbs energy of binding of A77003 to the wild type protease and the resistant mutant V84A. $\Delta\Delta G$ is calculated as $(\Delta G_{mutant} - \Delta G_{wild\ type})$ for all residues that contribute more than 0.1 kcal/mol to the binding free energy.

The inhibition constants for A77003 to some mutants have been measured (Kaplan et al., 1994) and there is one case for which the crystallographic structure of the complex is also available; the complex of A77003 with the V82A mutant HIV-1 protease (Baldwin et al., 1995). Structure-based thermodynamic calculations were performed on the mutant complex resulting in a binding free energy of −12394 cal/mol compared with the value of −13167 cal/mol obtained for the wild type. These free energies translate into a 3.7-fold reduction in the binding affinity for the mutant which compares favorably with the 4-fold reduction measured experimentally (Baldwin et al., 1995). More important than the numerical comparison is the mechanism by which a single mutation affects the binding affinity. The structural mapping of the binding energetics in the wild and mutant complexes reveals that the effect of the mutation cannot be assigned to a single site and that the Gibbs free energy of binding is redistributed throughout the entire binding pocket. This result is in agreement with the crystallographic analysis of Baldwin et al. (Baldwin et al., 1995) who also concluded that the effect of the V82A mutation cannot be rationalized by the deletion of a single methyl group in each chain, and that the overall effect is due to the backbone rearrangement induced by that mutation. FIG. 14 shows the calculated ΔΔG values between mutant and wild type for all residues that contribute more than 0.1 kcal/mol to the binding free energy. This case illustrates very clearly that even for the replacement of a single methyl group, the Gibbs energy of binding cannot be rationalized by simply adding group contributions. Contributions such as those tabulated in Table 2 depend on the global context of each group. It also indicates that the interpretation of the effect of mutations on the binding affinity of an inhibitor requires a global analysis even if the mutation is located in the binding pocket.

The free energy of inhibitor binding to the protease molecule reflects a delicate balance between mutually compensatory enthalpy and entropy terms. These compensatory terms define the main thermodynamic roadblocks in molecular design. Molecular modifications resulting in a more favorable enthalpy bring about unfavorable entropy contributions, a phenomenon known as enthalpy-entropy compensation. Also, the enthalpy and entropy changes themselves are composed of opposing contributions. The enthalpy of formation of internal interactions is opposed by the enthalpy of desolvation, and the entropy of desolvation is opposed by the conformational entropy. Molecular design requires accurate prediction of these effects, in order to minimize the undesirable consequences of compensatory changes.

The high accuracy with which the binding affinities of a number of HIV-1 protease inhibitors can be predicted from structure suggests that the approach presented here can be used to help in the design of new protease inhibitors. In addition, given that the structural parameterization of the binding energetics accounts well for the observed change in inhibition constant between the wild type and a resistant mutant of the HIV-1 protease for which the high resolution structure is available, this approach has the potential for addressing the issue of resistance in molecular design.

EXAMPLE 2

Application of Structure-Based Thermodynamic Design of Peptide Inhibitors of the Aspartic Protease Endothiapepsin The development of a structure parameterization of the energetics of protein folding and binding (Bardi et al., 1997; D'Aquino et al., 1996; Gomez et al., 1995(a); Gomez et al., 1995(b); Hilser et al., 1996(b); Luque et al., 1996) has been shown to be accurate enough to predict the helical propensities of amino acids with an accuracy better than 0.2 kcal/mol (Luque et al., 1996), to correctly predict the global stability of proteins and the stability constants per residue as reflected in the pattern of NMR-detected hydrogen exchange protection factors (Hilser et al., 1996(c); Hilser et al., 1997(a); Hilser et al., 1997(b)), and to predict the binding affinity of thirteen HIV-1 protease inhibitors for which high resolution structures are available with an accuracy better than ±1 kcal/mol (Bardi et al., 1997). Since the parameterization has reached the state in which accurate prediction of protein folding energetics or binding affinities appears possible, it seems appropriate to begin the development of molecular design strategies based upon those thermodynamic principles.

The aspartic proteinases comprise a large family of widely distributed enzymes found in vertebrates, fungi, plants and retrovirus. Some members of the family have become the focus of increasing interest due to their medical relevance, e.g., the HIV protease encoded by the human immunodeficiency virus which plays a crucial role in the maturation of the virus, renin which plays an important role in blood pressure regulation, cathepsin D, a key enzyme in the intracellular degradation of proteins and suspected to be involved in processes such as protein catabolism, antigen processing, degenerative diseases and breast cancer progression, etc. Previously, we have shown that endothiapepsin is a well behaved model for the thermodynamic analysis of aspartic proteases (Gomez et al., 1995(b)). In particular, the association of the general inhibitor of aspartic proteases, pepstatin A, has been studied in great detail with this protein (Gomez et al., 1995(b)). In addition, the crystallographic structures of the complex of endothiapepsin with pepstatin A, as well as the free protein are known (Bailey et al., 1993; Blundell et al., 1990), thus facilitating the application and testing of structure-based design strategies discussed herein.

In the example presented here, a simple minimization algorithm has been implemented to identify the sequence of a peptide ligand that satisfies a predefined binding criteria. The starting point of this algorithm is the high resolution structure of the peptide/protein complex which is used as a template for mutations and conformational analysis. The successful application of this algorithm to the association of pepstatin A and endothiapepsin demonstrates that the structural parameterization of the energetics can be used in rational molecular design.

This example deals with the modification of a peptide ligand and the design of peptide variants that exhibit different binding affinities for the target protein. Two non-mutually exclusive procedures are considered. Mutations in sequence by replacing side chains at existing positions in the peptide, and alteration of peptide chain length by addition or deletion of amino acids. In all cases, the starting point is a peptide/protein complex for which the high resolution structure is known. It is assumed that the overall structure of the mutated complex remains essentially unchanged and that the effects of a mutation are restricted to its immediate surroundings.

Figure 15A:
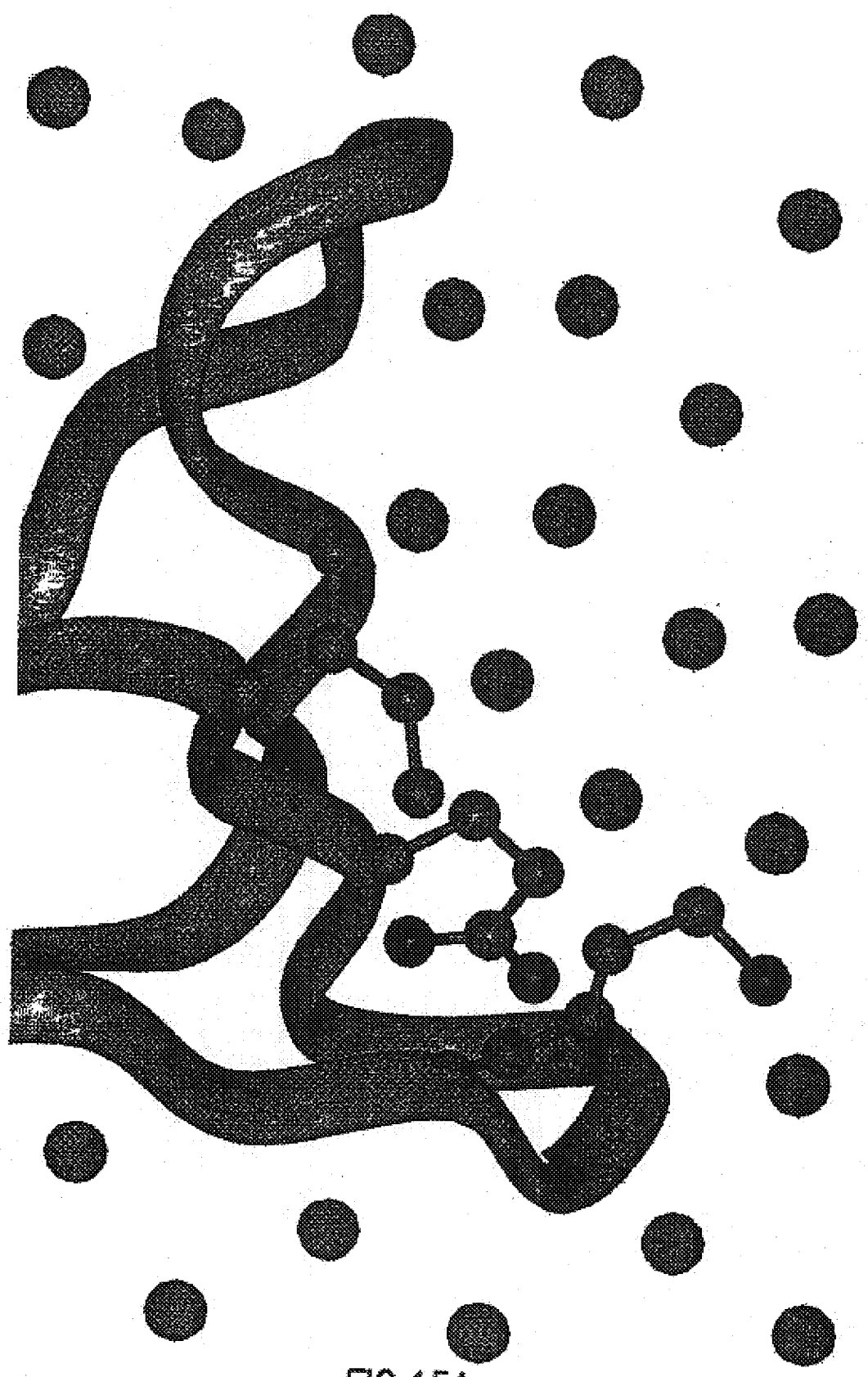
FIGS. 15A and 15B show two different conformations of a hypothetical side chain.
Figure 15B:
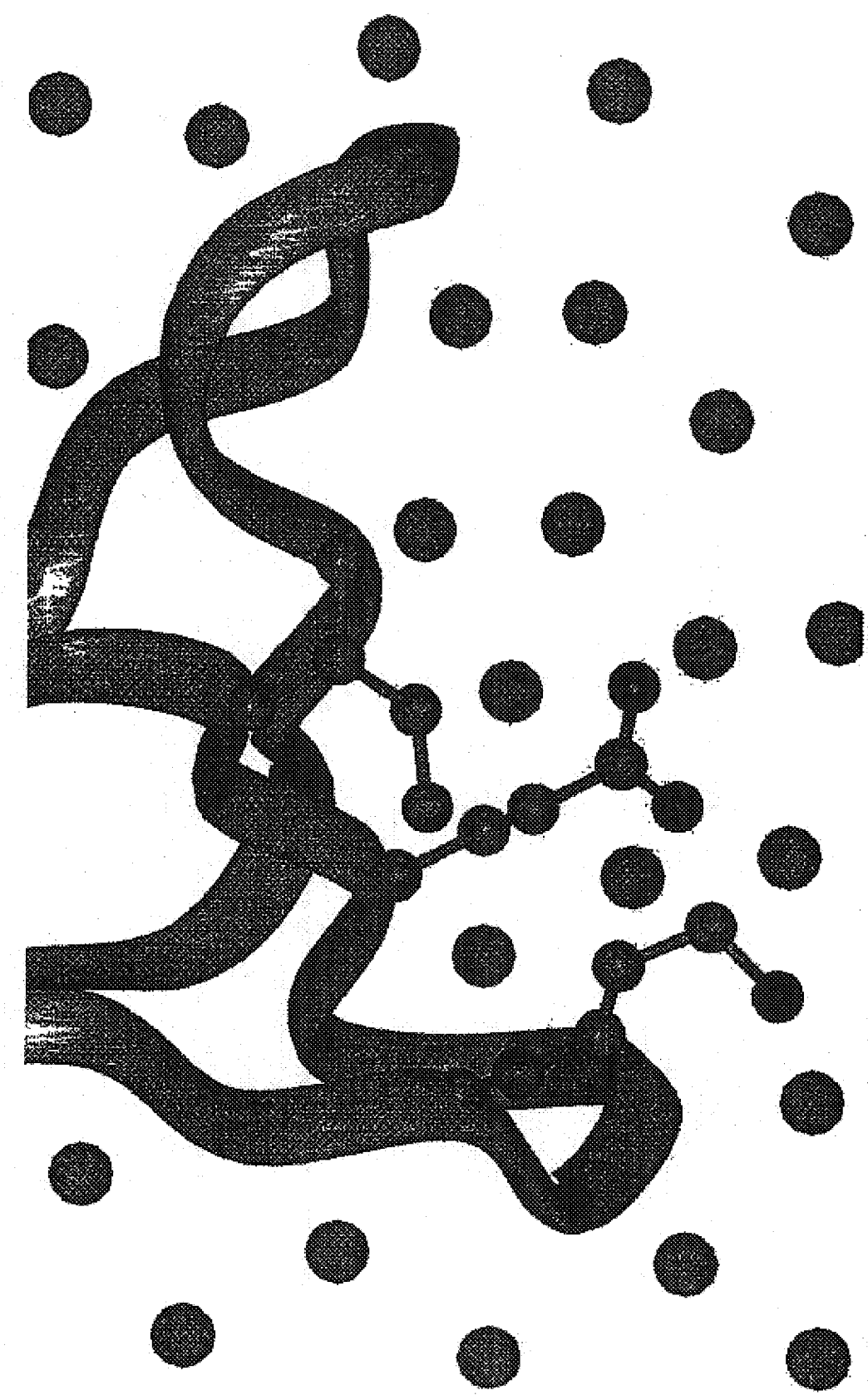

Once the mutation is made it is necessary to sample the ensemble of possible conformations and evaluate the energy and corresponding probability of each conformation. The probability of a single peptide conformation, defined by a specific set of side chain and backbone coordinates, is dictated by a Gibbs energy function, $\Delta G_{ef}$, specified by the enthalpy of intra and intermolecular peptide/protein interactions plus the enthalpy and entropy of solvation. $\Delta G_{ef}$ is a function of the side chain and backbone torsional angles. By definition, the conformational entropy of the peptide itself does not enter into the equation. $\Delta G_{ef}$ is the Gibbs energy function or Gibbs potential function of a single conformation and should not be confused with the Gibbs energy of binding which includes all permissible conformations. The situation is illustrated in FIGS. 15A and 15B for two hypothetical conformations of a side chain. These conformations exhibit not only different intramolecular interactions but also different degrees of solvation that define the Gibbs energy function, $\Delta G_{ef}$. The probability of any given conformation is given by the equation $$P_i = \frac{e^{-\Delta G_{ef,i}/R \cdot T}}{\sum_j e^{-\Delta G_{ef,j}/R \cdot T}}$$

where $e^{-\Delta G_{ef,i}}/RT$ is the Boltzmann exponent for that conformation, and the sum in the denominator is the conformational partition function defined as the sum of the Boltzmann exponents of all conformations. The Gibbs potential function, $\Delta G_{ef}$, is used to identify the most probable conformation of a side chain or backbone. For any given conformation $\Delta G_{ef}$ is calculated from structure using the structural parameterization of the energetics described before (Bardi et al., 1997; Gomez et al., 1995(a); Gomez et al., 1995(b); D'Aquino et al., 1996; Hilser et al., 1996(b); Luque et al., 1996) without including the conformational entropy.

Side chain conformations are generated by systematically varying the dihedral angles between 0° and 360° ($\chi_1$ for Cys, Ser, Thr and Val; $\chi_1$ and $\chi_2$ for Asn, Asp, His, Ile, Leu, Phe, Trp, Tyr; $\chi_1$, $\chi_2$ and $\chi_3$ for Gln, Glu, Met; $\chi_1$, $\chi_2$, $\chi_3$ and $\chi_4$ for Lys; and, $\chi_1$, $\chi_2$, $\chi_3$, $\chi_4$ and $\chi_5$ and for Arg). For those side chains with a single dihedral the value of $\chi_1$ is varied every degree, for chains with up to three dihedrals every 10°, and for higher numbers every 30°. For backbone conformations the torsional angles $\phi$ and $\psi$ are also varied every 10° between 0° and 360°.

Refinements can be made by identifying conformations that are close to an energy minimum and reduce the rotation intervals. Not every conformation generated in this way is feasible due to steric hindrances. For each conformation, van der Waals collisions are checked by using the set of effective van der Waals radii MMII published by Iijima et al. (Calibration of effective van der Waals contact radii for proteins and peptides, Protein, 2:330–339, 1987). Those conformations that exhibit van der Waals collisions are rejected. The Gibbs potential function $\Delta G_{ef}$ is calculated only for allowed conformations. This minimization algorithm has been implemented in the computer program CALVIN.

Figure 16:
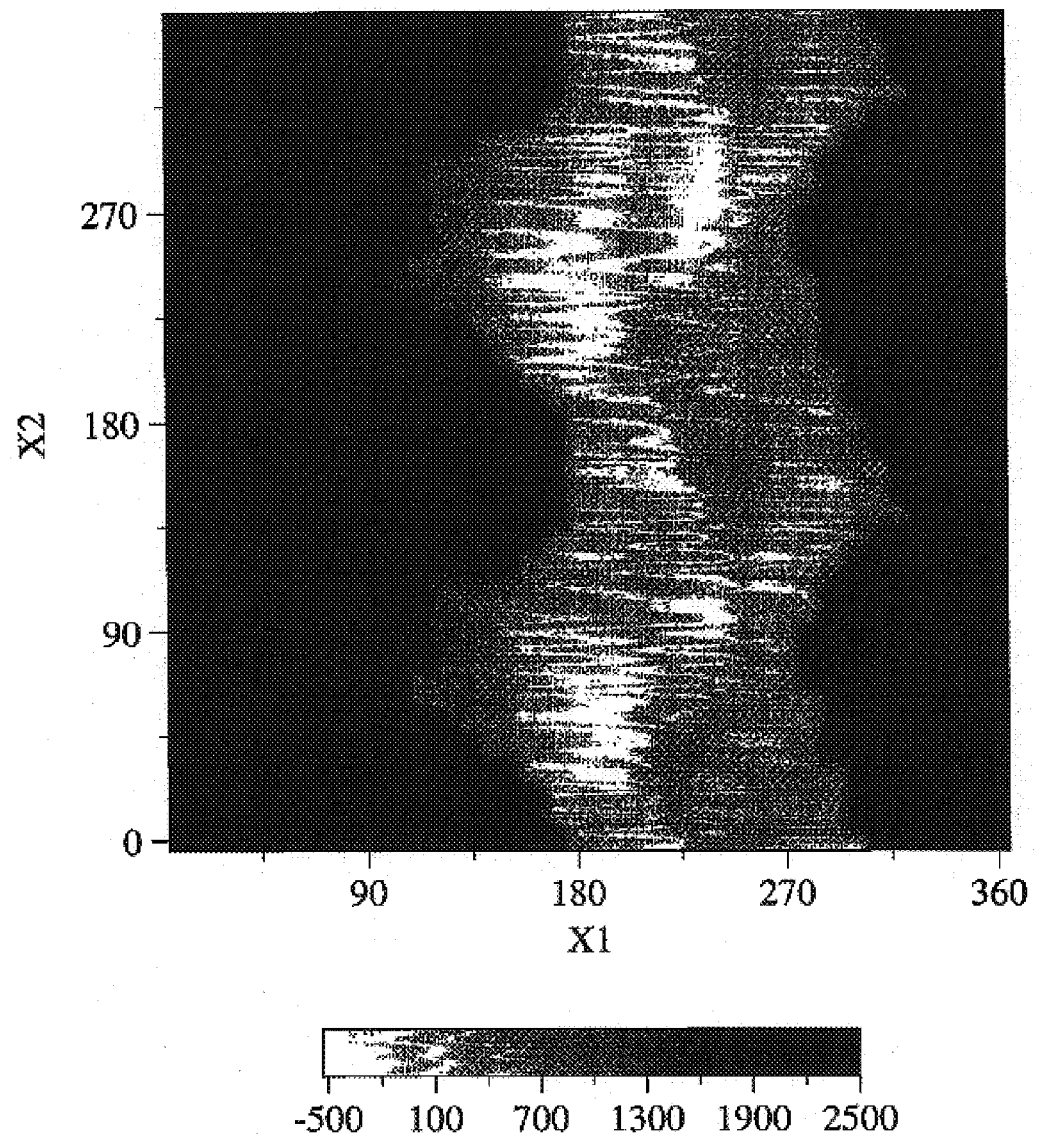
FIG. 16 is a energy profile for a solvent exposed phenylalanine side chain in a a-helix conformation as a function of the side chain dihedrals $\chi_1$ and $\chi_2$.

The ability of the structural parameterization to correctly locate energy minima was tested by applying the minimization algorithm to the optimization of side chain conformations in central positions of exposed alpha helices. The resulting energy profiles and in particular the location of the minima and subminima were well characterized by the algorithm and in good agreement with those published before (Janin et al., 1978; Lee et al., 1994). The results obtained for phenylalanine are illustrated in FIG. 16.

Generation of Mutated Peptides

In all cases, the coordinate sets for the complexes between the protein and the mutated peptides are generated by using the coordinates of the wild type complex as a template. Replacement mutants are created by replacing the original side chain with the desired mutation, leaving the backbone in the original conformation. For mutations that involve the addition of an extra amino acid at either end of the peptide chain, the backbone torsional angles are also included in the minimization.

Pepstatin A (Iva-Val-Val-Sta-Ala-Sta, where Iva stands for isovaleric acid), is a potent and naturally occurring aspartic proteinase inhibitor. The inhibitor contains two residues of the unusual amino acid statine (Sta: 4(S)-amino-3(S)-hydroxy-6methylheptanoic acid). The central statine acts as a non-hydrolyzable transition-state analog of the two residues contributing to the scissile peptide bond in the substrate. Two different mutations of pepstatin A were studied. In the first one, Ala 5 which we identified before as being a weak contributor to the Gibbs energy of binding (Gomez et al., 1995(b)) was targeted for replacement. Twelve possible mutations at this position were considered (Cys, Gly, His, Ile, Leu, Met, Phe, Ser, Thr, Trp, Tyr, Val). For each of these mutations, the most probable conformation was identified. In the second case, the addition of an amino acid at the carboxy terminus of pepstatin A was considered. In this case, a simultaneous optimization of side chain and backbone conformations was performed in order to identify the most probable conformation.

Calculation of Binding Affinities

The binding affinity of the peptide for the protein is dictated by the Gibbs energy of binding which is calculated from the structures of the complex, the free protein and the free peptide as described before (Bardi et al., 1997; D'Aquino et al., 1996; Gomez et al., 1995(a); Gomez et al., 1995(b); Hilser et al., 1996(b); Luque et al., 1996). For each mutant complex the atomic coordinates corresponding to the conformation that minimizes the Gibbs potential function were used. For the free peptides the solvent accessibilities correspond to a Boltzmann weighted average of side chain and backbone conformations (Luque et al., 1996).

Figure 17:
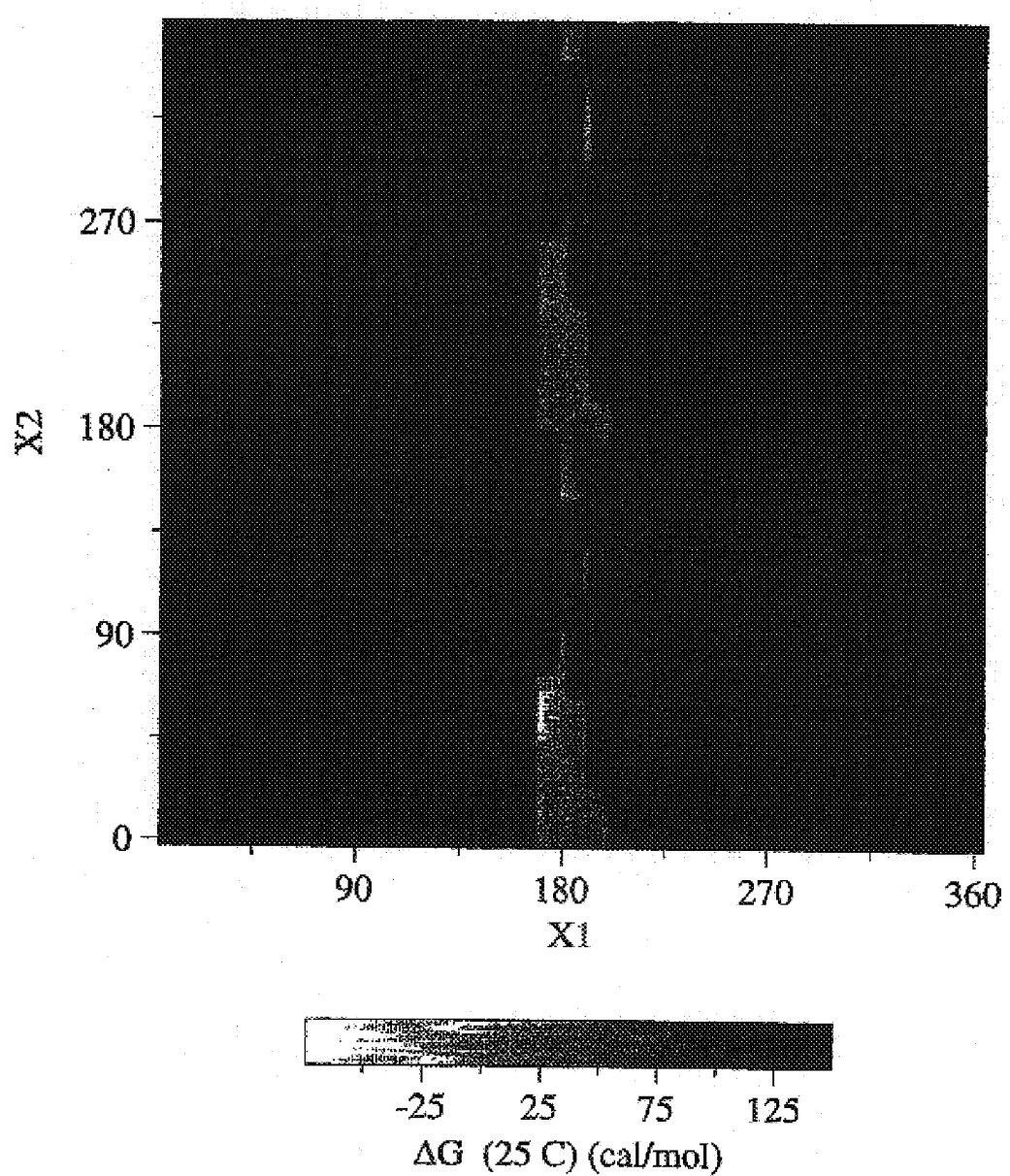
FIG. 17 is a calculation of the Gibbs potential profile as a function of the side chain dihedrals $\chi_1$ and $\chi_2$ for the phenylalanine at position 5 in the A5F mutant of pepstatin A.

FIG. 17 shows the Gibbs potential profile as a function of the $\chi_1$ and $\chi_2$ side chain dihedrals for the A5F mutant. It is clearly seen that the aromatic ring is essentially locked into a narrow set of $\chi_1$ values while it has a finite probability to sample a wider range of $\chi_2$ values. The probabilities along the $\chi_1$ and $\psi_2$ are determined by a Boltzmann statistics defined in terms of the Gibbs potential of each conformation. Along the $\chi_1$ and $\psi_2$ axis, the Gibbs potential profile shows a well defined minimum at 169° and 51° respectively.

Figure 18:
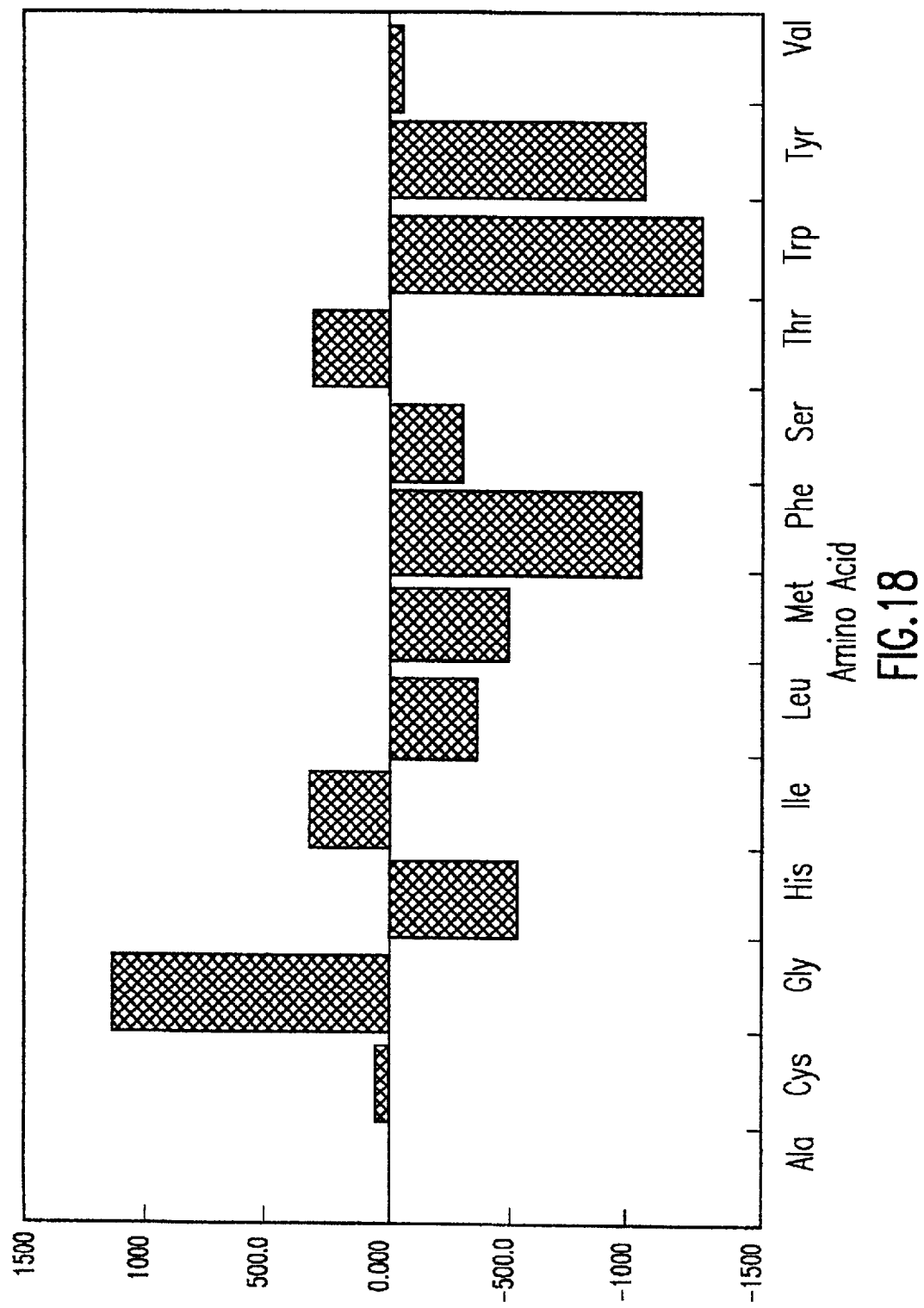
FIG. 18 is a calculation of the $\Delta\Delta G(25)$ values for twelve different mutants of pepstatin A at position five. $\Delta\Delta G(25)$ is the difference in binding Gibbs energy to endothiapepsin between the mutant and wild type inhibitor at 25° C. ($\Delta\Delta G(25) = \Delta G_{mut}(25) - \Delta G_{wild}(25)$).

FIG. 18 summarizes the expected differences in Gibbs energies calculated for the different amino acid mutations at position 5. The $\Delta\Delta G$ values are relative to the wild type. It is clear in the graph that the aromatic amino acids (Phe, Trp and Tyr) are predicted to elicit the largest increase in binding affinity. The predicted binding constants for the three aromatic amino acids are within 0.2 kcal/mol, which is below the expected prediction uncertainty and cannot be considered statistically significant. To test the structure-based thermodynamic prediction, the A5F mutant of pepstatin A was synthesized and the overall inhibition constant determined experimentally. As shown in Table 3, in accordance with the predicted behavior the A5F mutant binds to endothiapepsin more tightly than pepstatin A itself. Its predicted binding constant, $7.4 \times 10^9$ $M^{-1}$, is very close to the experimentally determined one, $5.3 \times 10^9$ $M^{-1}$, and the deviation of $\Delta G$ from its predicted value (0.2 kcal/mol) is within experimental error. Unfortunately, since the A5F mutant is more hydrophobic than the wild type pepstatin A and exhibits low water solubility, a direct calorimetric measurement of the binding enthalpy and heat capacity change was not possible in this case.

The second mutation considered in this study involved the addition of an amino acid at the carboxy terminus of the peptide. In order to improve the peptide solubility and facilitate the calorimetric analysis, it was decided to add a glutamate residue despite the prediction of a lower binding affinity. At 16° C., the binding of this inhibitor was exothermic and characterized by an enthalpy change ($\Delta H$) of $-4.6 \pm 0.1$ kcal/mol. The heat capacity change ($\Delta C_p$) obtained from the temperature dependence of the binding enthalpy change was equal to $-260 \pm 20$ cal/K•mol. For comparison, the calculated heat capacity from the derived structure is $-220$ cal/K•mol, and the generic enthalpy change, excluding protonation effects is $-6.8$ kcal/mol. These values are of the same order as the ones measured for pepstatin A under the same conditions ($\Delta H = -4.1$ kcal/mol and $\Delta C_p = -310$ cal/K•mol)$^2$. This result indicates that the main difference in binding affinities between the wild type and the E7 addition mutant is primarily entropic.

Experimental and calculated thermodynamic parameters for pepstatin A and the two mutations are summarized in Table 3. As predicted, the A5F mutant has a higher affinity than the wild type pepstatin A, while the E7 addition mutant has a lower affinity than the wild type. The agreement between predicted and experimental $\Delta G$ values is excellent. The average difference between predicted and experimental $\Delta G$ is $0.23 \pm 0.06$ kcal/mol. This result indicates that the structure-based parameterization of the energetics has enough sensitivity and resolution for peptide design.

For endothiapepsin, the high resolution structures of the protein in its free and bound forms are known, and accurate calculations of binding affinities are possible. In many cases, however, only the structure of the complex is known. If this is the case, the binding Gibbs energies of the mutants relative to the wild type can still be calculated with the same accuracy, and therefore peptide design can be done with the same precision. This situation holds even if there is a significant conformational change between the free and complexed proteins.

Structural Mapping of Binding Energetics

Figure 19A:
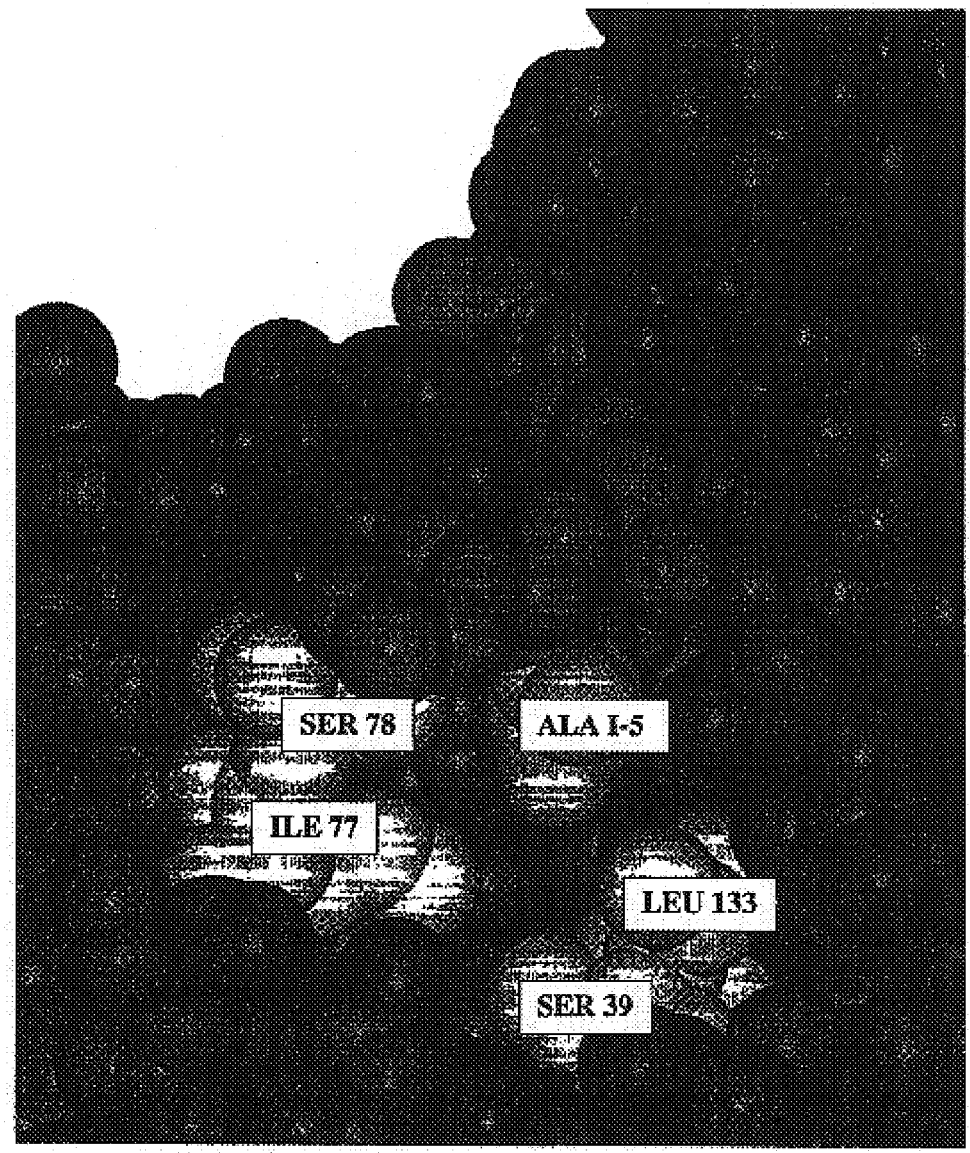
FIGS. 19A and 19B display the location of Ala 5 of pepstatin A in the complex with endothiapepsin and the situation predicted for the mutant A5F, respectively.
Figure 19B:
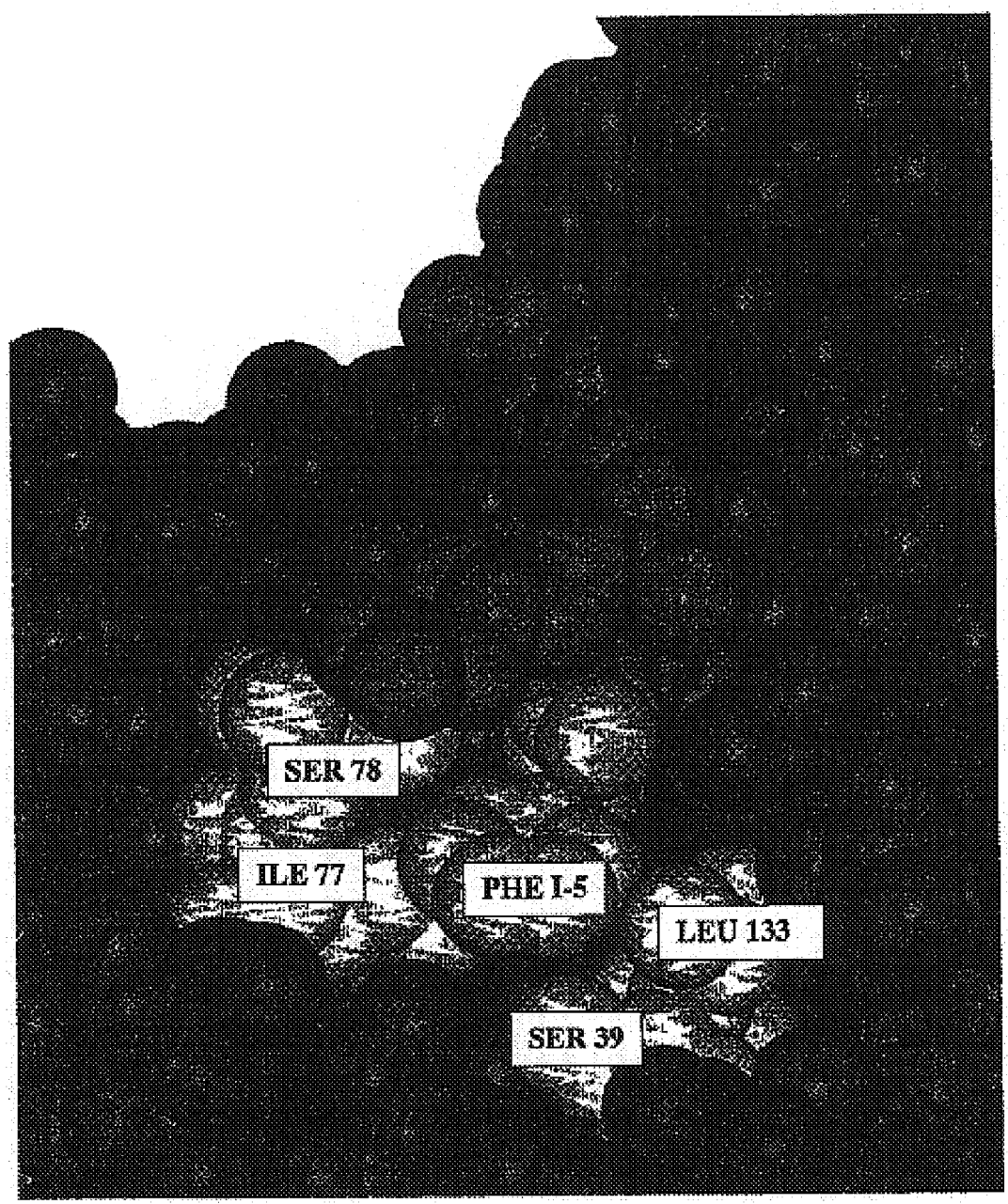

In pepstatin A, the alanine residue at position 6 is located in a relatively large hydrophobic pocket without making good van der Waals contacts with the enzyme and without burying a significant surface from the solvent (FIG. 19A). Phe, Tyr and Trp are predicted to exhibit a higher affinity because the aromatic ring of these amino acids partially fits in that cavity and optimizes the interactions with Leu 133, Ser 78, Ile 77 and Ser 39 as shown in FIG. 19B. Even though the aromatic ring of the phenylalanine is only partially buried, the interactions and the additional desolvation exhibited by Leu 133, Ser 78, Ile 77 and Ser 39 provide most of the additional Gibbs energy of binding.

The Gibbs energy of binding of the A5F mutant is about 1 kcal/mol more favorable than the wild type. The contribution due to the additional desolvation entropy arising from the burial of a larger number of hydrophobic groups is close to 4 kcal/mol. However, this entropic contribution is partially compensated by a less favorable enthalpy change (~2 kcal/mol more positive for A5F) and a larger conformational entropy loss (~1 kcal/mol) due to additional restrictions in side chain degrees of freedom upon complex formation. The enthalpy change for A5F is less favorable than for the wild type because the additional desolvation enthalpy cannot be completely compensated by the additional interactions between the peptide and protease molecule. As is the case in all binding processes, several compensating interactions occur simultaneously:

1) enthalpy/entropy compensation;
2) enthalpic compensation between solvation/intermolecular interactions; and,
3) entropic compensation between solvation and conformational entropy.

As a result, the overall free energy change is smaller than the isolated contributions.

Figure 20:
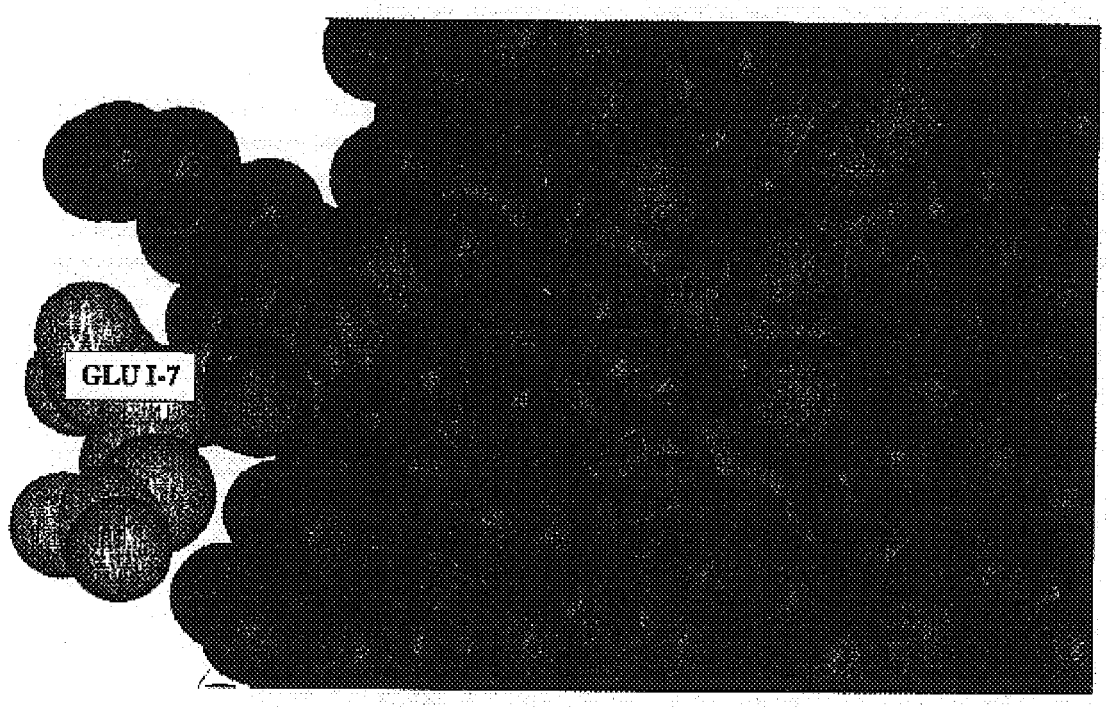
FIG. 20 displays the predicted location of Glu 7 of pepstatin A in the complex with endothiapepsin.

In the case of the E7 mutant, the length of the peptide has been increased at the carboxy terminus. The additional glutamate is pointing outward from the body of the protein and does not interact significantly with any residue. This is reflected in the similar enthalpies and heat capacities observed for this mutant and the wild type pepstatin A. The difference in binding Gibbs energies is mainly entropic and due primarily to the loss of conformational entropy of the glutamate upon binding. This loss of conformational entropy is not compensated by a favorable interaction either enthalpic or entropic, and results in a significant increase in $\Delta G$ and consequent loss of binding affinity. FIG. 20 shows the predicted location of the glutamate residue.

The results presented here demonstrate that the structural parameterization of the energetics developed earlier in this laboratory (Bardi et al., 1997; D'Aquino et al., 1996; Gomez et al., 1995(a); Gomez et al., 1995(b); Hilser et al., 1996(b); Luque et al., 1996) has the necessary accuracy and resolution to be used in minimization algorithms for molecular design. The algorithm described here has permitted the design of two mutant peptides which exhibit experimental binding energies similar to those predicted computationally. The success of this procedure validates the use of this approach in the design of peptide ligands.

Implementation

The methods and mechanisms described here are not limited to any particular hardware or software configuration, but rather they may find applicability in any computing or processing environment used in connection with online computer services.

The invention may be implemented in hardware or software, or a combination of both. However, preferably, the invention is implemented in computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the present invention have been described. Nevertheless, it will be understood that various modifications may be made without departing from the spirit and scope of the invention. Accordingly, other embodiments are within the scope of the claims.

TABLE I

Structure-based Thermodynamics of Inhibitor Binding to HIV-1 Protease[a]

| Inhibitor | $\Delta C_p$ | $\Delta H_{gen}$ | $\Delta S_{solv}$ | $\Delta S_{conf}$ | $\Delta G_{gen}$ | $\Delta G_{other}$ | $\Delta G_{Total}$ | $\Delta\Delta G$ |
|---|---|---|---|---|---|---|---|---|
| A77003 | −397 | 11733 | 115.2 | −23.7 | −15552 | 2385 | −13167 | 532 |
| A78791 | −400 | 12183 | 115.8 | −24.2 | −15127 | 2385 | −12742 | 1557 |
| A76928 | −392 | 11853 | 113.4 | −23.6 | −14932 | 2385 | −12547 | 1249 |
| A74704 | −379 | 11254 | 110.1 | −20.8 | −15378 | 2953 | −12425 | −1037 |
| A76889 | −387 | 11303 | 112.7 | −23.7 | −15229 | 2680 | −12549 | −271 |
| VX478 | −320 | 8641 | 93.9 | −11.1 | −16046 | 2903 | −13143 | −563 |
| SB203386 | −343 | 10410 | 96.2 | −16.8 | −13263 | 2555 | −10688 | −123 |
| SB203238 | −320 | 8641 | 94.0 | −18.1 | −13959 | 2918 | −11041 | −2356 |
| SB206343 | −332 | 8109 | 98.9 | −19.8 | −15481 | 2724 | −12757 | −177 |
| U100313 | −317 | 8471 | 93.4 | −16.6 | −14416 | 2807 | −11608 | −1531 |
| U89360 | −236 | 1255 | 76.5 | −28.0 | −13211 | 2877 | −10334 | −893 |
| A98881 | −293 | 8512 | 86.6 | −1.0 | −18018 | 2615 | −15403 | 14 |
| CGP53820 | −294 | 6294 | 88.7 | −22.3 | −13504 | 2643 | −10861 | 115 |

[a]Calculated thermodynamic parameters for inhibitor binding to HIV-1 protease. $\Delta C_p$ is in cal/K · mol; $\Delta S$ values are in cal/K · mol; $\Delta H$ and $\Delta G$ values are in cal/mol. $\Delta H_{gen}$ and $\Delta G_{gen}$ include only the structure/solvation contributions to $\Delta G$. Under $\Delta G_{other}$ the elctrostatic and cratic contributions have been combined.

TABLE II

Mapping of HIV-1 Residue Contributions to Gibbs Energy of Inhibitor Binding[a]

| Residue | A77003 | A78791 | A76928 | A74704 | A76889 | VX478 |
|---|---|---|---|---|---|---|
| ARG_8_A | −351 | −358 | −397 | −602 | −385 | −132 |
| ASP_25_A | −344 | −351 | −342 | −146 | −377 | −283 |
| GLY_27_A | −778 | −747 | −579 | −629 | −596 | −538 |
| ALA_28_A | −189 | −178 | −207 | −192 | −209 | −146 |
| ASP_29_A | −435 | −447 | −407 | −702 | −413 | −312 |
| ASP_30_A | −198 | −248 | −192 | −184 | −232 | −110 |
| MET_46_A | 0 | 0 | 0 | −290 | 0 | 0 |
| ILE_47_A | −43 | −39 | −38 | −146 | −30 | −84 |
| GLY_48_A | −965 | −962 | −906 | −935 | −933 | −719 |
| GLY_49_A | −351 | −378 | −265 | −173 | −241 | −125 |
| ILE_50_A | −271 | −294 | −253 | −185 | −272 | −239 |
| PHE_53_A | 0 | 0 | 0 | −91 | 0 | 0 |
| PRO_81_A | −121 | −129 | −152 | −166 | −160 | −78 |
| VAL_82_A | −351 | −357 | −347 | −191 | −359 | −119 |
| ILE_84_A | −86 | −64 | −82 | −67 | −83 | −99 |
| ARG_8_B | −505 | −513 | −376 | −230 | −462 | −245 |
| ASP_25_B | −323 | −345 | −369 | −315 | −366 | −273 |
| GLY_27_B | −648 | −652 | −590 | −501 | −561 | −594 |
| ALA_28_B | −184 | −189 | −196 | −237 | −195 | −146 |
| ASP_29_B | −473 | −478 | −377 | −432 | −404 | −275 |
| ASP_30_B | −167 | −164 | −156 | −88 | −149 | −273 |
| ILE_47_B | −56 | −53 | −60 | −75 | −59 | −73 |

TABLE II-continued

Mapping of HIV-1 Residue Contributions to Gibbs Energy of Inhibitor Binding[a]

| | | | | | | |
|---|---|---|---|---|---|---|
| GLY_48_B | −968 | −954 | −906 | −1413 | −931 | −507 |
| GLY_49_B | −156 | −189 | −191 | −201 | −185 | −150 |
| ILE_50_B | −319 | −256 | −263 | −125 | −261 | −215 |
| PRO_81_B | −247 | −233 | −154 | −133 | −179 | −153 |
| VAL_82_B | −398 | −388 | −352 | −151 | −393 | −142 |

| Residue | SB203386 | SB203238 | SB206343 | U100313 | U89360 | A98881 | CGP53820 |
|---|---|---|---|---|---|---|---|
| ARG_8_A | −311 | −468 | −228 | −106 | −140 | −363 | −425 |
| ASP_25_A | −320 | −283 | −248 | −313 | −346 | −290 | −312 |
| GLY_27_A | −810 | −436 | −775 | −437 | −703 | −542 | −789 |
| ALA_28_A | −165 | −207 | −159 | −181 | −135 | −195 | −177 |
| ASP_29_A | −197 | −455 | −422 | −308 | −570 | −331 | −336 |
| ASP_30_A | −158 | −137 | −220 | −382 | −437 | −187 | −202 |
| MET_46_A | 0 | 0 | 0 | 0 | −17 | 0 | 0 |
| ILE_47_A | −46 | −78 | −87 | −107 | −97 | −77 | −55 |
| GLY_48_A | −592 | −616 | −1081 | −1021 | −1186 | −821 | −904 |
| GLY_49_A | −155 | −128 | −140 | −192 | −282 | −107 | −253 |
| ILE_50_A | −260 | −167 | −271 | −210 | −151 | −235 | −231 |
| PHE_53_A | 0 | 0 | −65 | −69 | −161 | 0 | 0 |
| PRO_81_A | −131 | −181 | −123 | −42 | −97 | −98 | −148 |
| VAL_82_A | −200 | −179 | −165 | −95 | −211 | −159 | −120 |
| ILE_84_A | −60 | −102 | −90 | −71 | −95 | −73 | −51 |
| ARS_8_B | −214 | −283 | −764 | −624 | −418 | −352 | −486 |
| ASP_25_B | −225 | −275 | −334 | −384 | −372 | −337 | −367 |
| GLY_27_B | −722 | −444 | −832 | −353 | −755 | −451 | −729 |
| ALA_28_B | −203 | −243 | −183 | −198 | −167 | −180 | −183 |
| ASP_29_B | −360 | −523 | −589 | −420 | −24 | −218 | −294 |
| ASP_30_B | −326 | −427 | −313 | −267 | 0 | −270 | −188 |
| ILE_47_B | −68 | −110 | −60 | −91 | −32 | −58 | −66 |
| GLY_48_B | −966 | −1089 | −846 | −701 | −433 | −591 | −958 |
| GLY_49_B | −166 | −216 | −192 | −170 | −174 | −144 | −150 |
| ILE_50_B | −193 | −204 | −362 | −215 | −216 | −212 | −305 |
| PRO_81_B | −126 | −76 | −219 | −362 | −348 | −122 | −160 |
| VAL_82_B | −179 | −134 | −156 | −215 | −121 | −135 | −94 |

[a]Gibbs energies are in cal/mol.

TABLE III

Experimental and Calculated Binding Gibbs Energies for Mutants of Pepstatin A

| Inhibitor | $\Delta G(25)_{cal}$ kcal/mol | $\Delta G(25)exp$ kcal/mol | $K_{b,calc}$ $M^{-1}$ | $K_{b,exp}$ $M^{-1}$ |
|---|---|---|---|---|
| Pepstatin A Iva-Val-Val-Sta-Ala-Sta | −12.5 | −12.7 | $1.5 \times 10^9$ | $2.3 \times 10^9$ |
| Iva-Val-Val-Sta-Phe-Sta | −13.5 | −13.3 | $7.4 \times 10^9$ | $5.3 \times 10^9$ |
| Iva-Val-Val-Sta-Ala-Sta-Glu | −11.8 | −11.3 | $4.5 \times 10^8$ | $2.1 \times 10^8$ |

REFERENCES

Abdel-Meguid, S. S. et al., *Biochem.*, 1994, 33:11671–11677.
Bailey et al., *Biochem.*, 1993, 289:363–371.
Baldwin et al., *Nature Struc. Biol.*, 1995, 2:244–249.
Baldwin, R. L., *Proc. Natl. Acad. Sci. USA*, 1986, 83:8069–8072.
Bardi et al., *Biochem.*, 1997, 36:6588–6596.
Blundell et al., *J. Mol. Biol.*, 1990, 211:919–941.
Brown et al., *Agric. Biol. Chem.*, 1990, 54:1563–1565.
Cabani et al., *J. Sol. Chem.*, 1981, 10:563–595.
Cha, S., *Biochem. Pharmac.*, 1975, 24:2177–2185.
Condra et al., *Nature*, 1995, 374:569–571.
DAquino et al., *Proteins*, 1996, 25:143–156.
Dunn et al., *Biochem. J.*, 1986, 237:899–906.
Erickson et al., *Science*, 1990, 249:527–529.
Fassler et al., *Bioorg. Med. Chem. Lett.*, 1993, 3:2817–2842.
Freire et al., *Anal. Chem.*, 1990, 62:950A–959A.
Freire et al., *J. Mol. Biol.*, 1991, 222:687–698.
Freire, E., *Archives Biochem. Biophys.*, 1993, 303:181–184.
García-Moreno et al., *Methods Enzymol.*, 1995, 259:512–538.
García-Moreno et al., *BioDhvs. Chem.* In Press, 1997.
Gomez et al., *Proteins: Structure, Function and Genetics*, 1995, 22:404–412.
Gomez et al., *J. Mol. Biol.*, 1995(b), 252:337–350.
Gomez et al., "Structure and Function of Aspartic Proteinases: Retroviral and Cellular Enzymes", (Eds. James, M.N.G.), Plenum Publishing Co., New York, 1997.
Hilser et al., *J. Mol. Bio.*, 1996(a), 262:756–772.
Hilser et al., *Proteins*, 1996(b), 26:123–133.
Hilser et al., *Proteins*, 1997(a), 27:171–183.
Hilser et al., *Biophysical Chem.*, 1997(b), 64:69–79.
Ho, D. D. et al., *J. Virol.*, 1994, 68, 2016–2020.
Hoog S. S. et al., *J. Med. Chem.*, 1995, 38, 3246–3252.
Hyland, L. J. et al., *Biochemistry*, 1991, 30, 8454–8463.
Ijima et al., *Proteins*, 1987, 2:330–339.
Janin et al., *J. Mol. Biol.*, 1978, 125:357–386.
Janin, J., *Proteins*, 1995, 21:30–39.

Kaplan et al., *Proc. Natl. Acad. Sci. USA,* 1994, 91:5597–5601.
Kauzmann, W., *Adv. Protein Chem.,* 1959, 14:1–63.
Kim et al., *J. Am. Chem. Soc.,* 1995, 117:1181–1182.
Kuzmic, P., Anal. Biochem., 1996, 237:260–273.
Larson et al., *J. Diary Sci.,* 1970, 53:253–262.
Lee et al., *J. Mol. Biol.,* 1971, 55:379–400.
Lee et al., *Proteins: Struct. Func. and Genetics,* 1994, 20:68–84.
Levitt, M., *J. Mol. Biol.,* 1974, 82:393–420.
Lin et al., *Biochem.,* 1993, 34:1143–1152.
Luque et al., *Biochemistry,* 1996, 35:13681–13688.
Luque et al., 1997 in press.
Madhusoodan et al., *J. Am. Chem. Soc.,* 1994, 116:847–855.
Murphy et al., *J. Mol. Biol.,* 1992(a), 227:293–306.
Murphy et al., *Adv. Protein Chem.,* 1992(b), 43:313–361.
Murphy et al., *Proteins: Struct. Func. Genetics,* 1993, 15:113–120.
Murphy et al., *Proteins: Struct. Func. Genetics,* 1994, 18:63–67.
Rich, D. H., in *Proteinase Inhibitors* (eds. Barret & Salvesen) (Elsevier Science Publishers, New York, 1986).
Rich et al., *Biochem. Pharmacol.,* 1980, 29.
Roberts, N. A., *AIDS,* 1995, 9:S27–S32.
Schellman, *Compt. Rend. Trav. Carlsburg, Ser. Chim.,* 1955 (a), 29:230–259.
Schellman, *C. R. Trav. Lab. Carlsburg Ser. Chim.,* 1955(b), 29:223–229.
Schinazi et al., *Int. Antiviral News,* 1996, 4:95–100.
Smith et al., *Nature Struc. Biol.,* 1996, 3:946–950.
Spinelli et al., *Biochimie,* 1991, 73:1391–1396.
Straume et al., "Thermodynamic Strategies for Protein Design: Increased Temperature Stability. In *Biocatalysis at Extreme Temperature: Enzyme Systems Near and Above* 100° C., (Adams, M. W. W. & Kelly R. M., eds.) 1992, pp. 122–135, ACS Books, Washington, D.C.
Thaisrivongs et al., *J. Med. Chem.,* 1995, 38:3624–3637.
Thompson et al., J. Med. Chem., 1994, 37: 3100–3107.
Tisdale, M., *Int. Antiviral News,* 1996, 4.
Wang et al., *Biochemistry,* 1996, 35:9945–9950.
Whitaker, J. R., *Methods in Enzymol.,* 1970, 19:436–445.
Williams et al., *Methods Enzymol,* 1979, 63:437–467.
Wiseman et al., *Anal. Biochem.,* 1989, 179:131–135.
Wlodawer et al., *Ann. Rev. Biochem.,* 1993, 62:543–585.
Xie et al., *Proteins: Struct. Func. Genetics,* 1994(a), 19:291–301.
Xie et al., *J. Mol. Biol.,* 1994(b), 24:62–80.

What is claimed is:

1. A computer-assisted method for predicting the binding affinity of a compound for a binding target of a molecule, using a programmed computer including a processor, an input device, and an output device, including the steps of:

i) inputting into the programmed computer, through the input device, data including the identity and three-dimensional coordinates of each of the atoms in the molecule;

ii) determining, using the processor, for each atom in the molecule, a predicted Gibbs free energy of binding of the atom to an ideal ligand;

iii) generating, using the processor, a three-dimensional prediction model of binding targets in the molecule by generating, using the three-dimensional coordinates of each of the atoms in the molecule, a model of the atoms in the molecule and mapping onto each atom depicted in the model the corresponding determined predicted Gibbs free energy of binding;

iv) identifying as a binding target a region of the molecule with a high density of atoms which exhibit favorable Gibbs free energy of binding to said ideal ligand, v) inputting into the programmed computer, through the input device, data including the identity and three-dimensional coordinates of each of the atoms in the binding target, vi) inputting into the programmed computer, through the input device, data including the identity and three-dimensional coordinates of each of the atoms in the compound;

vii) generating, using the processor, model of the compound bound to the binding target;

viii) determining, using the processor, the three-dimensional coordinates of an energy minimized structure of the compound when the compound is bound to the binding target; and ix) determining, using the processor, a predicted binding affinity of the energy minimized compound for the binding target.

2. A computer program, residing on a computer-readable medium, for predicting the binding affinity of a compound for a binding target of a molecule, the computer program including instructions for causing a computer to:

i) receive data including the identity and three-dimensional coordinates of each of the atoms in the molecule;

ii) determine, for each atom in the molecule, a predicted Gibbs tee energy of binding of the atom to an ideal ligand for the atom;

iii) generate a three-dimensional prediction model of binding targets in the molecule by generating, using the three-dimensional coordinates of each of the atoms in the molecule, a model of the atoms in the molecule and mapping onto each atom depicted in the model the corresponding determined predicted Gibbs free energy of binding;

iv) identify as a binding target a region of the molecule with a high density of atoms which exhibit favorable Gibbs free energy of binding to said ideal ligand, v) receive data including the identity and three-dimensional coordinates of each of the atoms in the binding target;

vi) receive data including the identity and three-dimensional coordinates of each of the atoms in the compound;

vii) generate a model of the compound bound to the binding target;

viii) determine the three-dimensional coordinates of an energy minimized structure of the compound when the compound is bound to the binding target; and ix) determine a predicted binding affinity of the energy minimized compound for the binding target.

3. A computer-assisted method for ranking each ligand in a act of ligands by its predicted binding affinities for binding to a binding target of a molecule, using a programmed computer including a processor, and input device, and an output device, including the steps of:

i) inputting into the programmed computer, through the input device, data including the identity and three-dimensional coordinates of each of the atoms in the molecule;

ii) determining, using the processor, for each atom in the molecule, a predicted Gibbs free energy of binding of the atom to an ideal ligand;

iii) generating, using the processor, a three-dimensional prediction model of binding targets in the molecule by generating, using the three-dimensional coordinates of each of the atoms in the molecule, a model of the atoms in the molecule and mapping onto each atom depicted in the model the corresponding determined predicted Gibbs free energy of binding;

iv) identifying as a binding target a region of the molecule with a high density of atoms which exhibit favorable Gibbs free energy of binding to said ideal ligand, v) inputting into the programmed computer, through the input device, data including the identity and three-dimensional coordinates of each of the atoms in the binding target, vi) inputting into the programmed computer, through the input device, data including the identity and three-dimensional coordinates of each of the atoms in each ligand in the set of ligands;

vii) generating, using the processor, a model of each ligand in the set of ligands bound to the binding target;

viii) determining, using the processor, the three-dimensional coordinates of an energy minimized structure of each ligand in the set of ligands when each ligand in the set of ligands is bound to the binding target;

ix) determining, using the processor, a predicted binding affinity of the energy minimized structure of each ligand in the set of ligands for the binding target; and x) ranking each ligand according to its determined predicted binding affinity.

4. A computer program, residing on a computer-readable medium, for ranking each ligand in a set of ligands by its predicted binding affinities for binding a binding target of a molecule, the computer program including instructions for causing a computer to:

i) receive data including the identity and three-dimensional coordinates of each of the atoms in the molecule;

ii) determine, using the processor, for each atom in the molecule, a predicted Gibbs free energy of binding of the atom to an ideal ligand;

iii) generate, using the processor, a three-dimensional prediction model of binding targets in the molecule by generating, using the three-dimensional coordinates of each of the atoms in the molecule, a model of the atoms in the molecule and mapping onto each atom depicted in the model the corresponding determined predicted Gibbs free energy of binding;

iv) identify as a binding target a region of the molecule with a high density of atoms which exhibit favorable Gibbs free energy of binding to said ideal ligand, v) receive data including the identity and three-dimensional coordinates of each of the atoms in the binding target, vi) receive data including the identity and three-dimensional coordinates of each of the atoms in each ligand in the set of ligands;

vii) generate, using the processor, a model of each ligand in the set of ligands bound to the binding target;

viii) determine, using the processor, the three-dimensional coordinates of an energy minimized structure of each ligand in the set of ligands when each ligand in the set of ligands is bound to the binding target;

ix) determine, using the processor, a predicted binding affinity of the energy minimized structure of each ligand in the set of ligands for the binding target; and x) rank each ligand according to its determined predicted binding affinity.

* * * * *